United States Patent
Gong et al.

(10) Patent No.: US 6,797,499 B2
(45) Date of Patent: Sep. 28, 2004

(54) ISOLATED HUMAN DEHYDROGENASES, NUCLEIC ACID MOLECULES ENCODING THESE HUMAN DEHYDROGENASES, AND USES THEREOF

(75) Inventors: Fangcheng Gong, Germantown, MD (US); Chunhua Yan, Boyds, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 38 days.

(21) Appl. No.: 10/118,037

(22) Filed: Apr. 9, 2002

(65) Prior Publication Data

US 2002/0160481 A1 Oct. 31, 2002

Related U.S. Application Data

(62) Division of application No. 09/740,028, filed on Dec. 20, 2000, now Pat. No. 6,410,289.

(51) Int. Cl.$^7$ ................................................. C12N 9/02
(52) U.S. Cl. ..................................................... 435/189
(58) Field of Search ......................................... 435/189

(56) References Cited

PUBLICATIONS

Wang, J., et al. (1999) Biochem. J. 338, 23–27.*
Simon, A., et al. (1996) Genomics 36, 424–430.*
Mertz. J.R., et al. (1997) J. Biol. Chem. 272(18), 11744–11749.*
Rattner A., et al. (2000) J. Biol. Chem. 278(15), 11034–11043.*
Results of BLAST search of SEQ ID No.:2 against Derwent (FastAlert and GeneSeqP) and NCBI (pataa) protein patent databases on Mar. 17, 2003.

* cited by examiner

*Primary Examiner*—Charles L. Patterson, Jr.
(74) *Attorney, Agent, or Firm*—Celera Genomics; Lin Sun-Hoffman

(57) ABSTRACT

The present invention provides amino acid sequences of polypeptides that are encoded by genes within the human genome, the dehydrogenase polypeptides of the present invention. The present invention specifically provides isolated polypeptide and nucleic acid molecules, methods of identifying orthologs and paralogs of the dehydrogenase polypeptides, and methods of identifying modulators of the dehydrogenase polypeptides.

8 Claims, 15 Drawing Sheets

```
   1 TGCTTCCGGA GCCGGAGGGG GCCCGGCGTA CCCAGCCCCC AGCCCGACGT
  51 GACCATGCTG TCCCGCCTCC TAAAAGAACA CCAGGCCAAG CAGAATGAAC
 101 GCAAGGAGCT GCAGGAAAAG AGGAGGCGAG AGGCTATCAC TGCAGCGACC
 151 TGCCTGACAG AAGCTTTGGT GGATCACCTC AATGTGGGTG TGGCCCAGGC
 201 CTACATGAAC CAGAGAAAGC TGGACCATGA GGTGAAGACC CTACAGGTCC
 251 AGGCTGCCCA ATTTGCCAAG CAGACAGGCC AGTGGATCGG AATGGTGGAG
 301 AACTTCAACC AGGCACTCAA GCTGGACCAG AGAGGCTTCC GAGTCCTGGC
 351 CAGCTGCCTG ACCCCCTCCG GGGCCGAGGA CCTGCAGCGG GTGGCCTCCT
 401 CCCGCCTCCA CACCACCCTG TTGGATATCA CTGATCCCCA GAGCGTCCAG
 451 CAGGCAGCCA AGTGGGTGGA GATGCACGTT AAGGAAGCAG GGCTTTTTGG
 501 TCTGGTGAAT AATGCTGGTG TGGCTGGTAT CATCGGACCC ACACCATGGC
 551 TGACCCGGGA CGATTTCCAG CGGGTGCTGA ATGTGAACAC AATGGGTCCC
 601 ATCGGGGTCA CCCTTGCCCT GCTGCCTCTG CTGCAGCAAG CCCGGGGCCG
 651 GGTGATCAAC ATCACCAGCG TCCTGGGTCG CCTGGCAGCC AATGGTGGGG
 701 GCTACTGTGT CTCCAAATTT GGCCTGGAGG CCTTCTCTGA CAGCCTGAGG
 751 CGGGATGTAG CTCATTTTGG GATACGAGTC TCCATCGTGG AGCCTGGCTT
 801 CTTCCGAACC CCTGTGACCA ACCTGGAGAG TCTGGAGAAA ACCCTGCAGG
 851 CCTGCTGGGC ACGGCTGCCT CCTGCCACAC AGGCCCACTA TGGGGGGGCC
 901 TTCCTCACCA AGTACCTGAA AATGCAACAG CGCATCATGA ACCTGATCTG
 951 TGACCCGGAC CTAACCAAGG TGAGCCGATG CCTGGAGCAT GCCCTGACTG
1001 CTCGACACCC CCGAACCCGC TACAGCCCAG GTTGGGATGC CAAGCTGCTC
1051 TGGCTGCCTG CCTCCTACCT GCCAGCCAGC CTGGTGGATG CTGTGCTCAC
1101 CTGGGTCCTT CCCAAGCCTG CCCAAGCAGT CTACTGAATC CAGCCTTCCA
1151 GCAAGAGATT GTTTTTCAAG GACAAGGACT TTGATTTATT TCTGCCCCCA
1201 CCCTGGTACT GCCTGGTGCC TGCCACAAAA TAAGCACTAA CAAAAGTGTA
1251 TTGTTTAAAA AATAAAAAGA AGGTGGGCAG AAATGTGCCC AGTGGAAAAA
1301 AAAAAAAAAA AAAAAAAAAA AAAAAAAAAA AAAAA (SEQ ID NO:1)
```

FEATURES:
5'UTR: 1 - 54
Start Codon: 55
Stop Codon: 1135
3'UTR: 1138

Homologous proteins:
```
gi|2492753|sp|Q92781|RDH1_HUMAN 11-CIS RETINOL DEHYDROGENASE (1...   558   e-158
gi|4506463|ref|NP_002896.1|    retinol dehydrogenase 5 (11-cisand ...  540   e-152
gi|2492752|sp|Q27979|RDH1_BOVIN 11-CIS RETINOL DEHYDROGENASE (1...   515   e-145
gi|2136691|pir||I45845 11-cis-retinol dehydrogenase (EC 1.1.1.-...    515   e-145
gi|2687587|gb|AAC00491.1| (AF033195) 9-cis-retinol dehydrogenas...    492   e-138
gi|9837274|gb|AAG00507.1|AF285079_1 (AF285079) 11-cis retinol d...   371   e-101
gi|4506571|ref|NP_003699.1| microsomal NAD+-dependent retinol d...   297   2e-79
gi|1710629|sp|P50169|ROH1_RAT RETINOL DEHYDROGENASE TYPE I (ROD...    297   2e-79
gi|1710630|sp|P50170|ROH2_RAT RETINOL DEHYDROGENASE TYPE II (RO...    297   2e-79
gi|841197|gb|AAB07997.1| (U18762) retinol dehydrogenase type I ...    297   2e-79
```

FIGURE 1A

EST
```
gb|BE221672|BE221672 hu27e10.x1 NCI_CGAP_Mel15 Homo sapiens cDN...   912  0.0
gb|AI609763|AI609763 tf83a04.x1 NCI_CGAP_Brn23 Homo sapiens cDN...   719  0.0
gb|AA618161|AA618161 nq14d10.s1 NCI_CGAP_Thy1  Homo sapiens cDNA...  687  0.0
gb|AA621911|AA621911 nq30b08.s1 NCI_CGAP_Co10  Homo sapiens cDNA...  632  e-178
gb|AW005857|AW005857 wz80d08.x1 NCI_CGAP_Gas4  Homo sapiens cDNA...  562  e-157
gb|BF238091|BF238091 601811810F1 NIH_MGC_48 Homo sapiens cDNA c...   530  e-148
gb|BE550980|BE550980 7b66g08.x1 NCI_CGAP_Lu24  Homo sapiens cDNA...  530  e-148
gb|BE396580|BE396580 601288811F1 NIH_MGC_8 Homo sapiens cDNA cl...   530  e-148
```

EXPRESSION INFORMATION FOR MODULATION USE:
gb|BE221672|   malignant melanoma, metastatic to lymph node
gb|AI609763|   brain - glioblastoma
gb|AA618161|   thyroid
gb|AA621911|   colon tumor RER+
gb|AW005857|   stomach -poorly differentiated adenocarcinoma with signet ring cell      features
gb|BF238091|   primary B-cells from tonsils
gb|BE550980|   lung carcinoid
gb|BE396580|   Burkitt lymphoma Tissue Expression:
Human leukocyte

FIGURE 1B

```
  1  MLSRLLKEHQ AKQNERKELQ EKRRREAITA ATCLTEALVD HLNVGVAQAY
 51  MNQRKLDHEV KTLQVQAAQF AKQTGQWIGM VENFNQALKL DQRGFRVLAS
101  CLTPSGAEDL QRVASSRLHT TLLDITDPQS VQQAAKWVEM HVKEAGLFGL
151  VNNAGVAGII GPTPWLTRDD FQRVLNVNTM GPIGVTLALL PLLQQARGRV
201  INITSVLGRL AANGGGYCVS KFGLEAFSDS LRRDVAHFGI RVSIVEPGFF
251  RTPVTNLESL EKTLQACWAR LPPATQAHYG GAFLTKYLKM QQRIMNLICD
301  PDLTKVSRCL EHALTARHPR TRYSPGWDAK LLWLPASYLP ASLVDAVLTW
351  VLPKPAQAVY (SEQ ID NO:2)
```

FEATURES:
Functional domains and key regions:
Prosite search results:
[1] PDOC00001 PS00001 ASN_GLYCOSYLATION
N-glycosylation site 202-205 NITS

---

[2] PDOC00005 PS00005 PKC_PHOSPHO_SITE
Protein kinase C phosphorylation site

Number of matches: 3
  1  115-117 SSR
  2  230-232 SLR
  3  315-317 TAR

---

[3] PDOC00006 PS00006 CK2_PHOSPHO_SITE
Casein kinase II phosphorylation site

Number of matches: 6
  1  105-108 SGAE
  2  121-124 TLLD
  3  167-170 TRDD
  4  243-246 SIVE
  5  255-258 TNLE
  6  342-345 SLVD

---

[4] PDOC00008 PS00008 MYRISTYL
N-myristoylation site

Number of matches: 8
  1   45-50  GVAQAY
  2   75-80  GQWIGM
  3   79-84  GMVENF
  4  149-154 GLVNNA
  5  184-189 GVTLAL
  6  214-219 GGGYCV
  7  239-244 GIRVSI
  8  281-286 GAFLTK

---

FIGURE 2A

Membrane spanning structure and domains:
```
Helix Begin  End  Score  Certainty
  1    145   165  1.041  Certain
  2    175   195  1.320  Certain
  3    333   353  0.949  Putative
```
BLAST Alignment to Top Hit:
```
>gi|2492753|sp|Q92781|RDH1_HUMAN 11-CIS RETINOL DEHYDROGENASE (11-CIS
        RDH)
 gb|AAC50725.1| (U43559) 11-cis retinol dehydrogenase [Homo sapiens]
 gb|AAC09250.1| (AF037062) retinol dehydrogenase [Homo sapiens]
        Length = 318

Score =  558 bits (1422), Expect = e-158
 Identities = 273/274 (99%), Positives = 274/274 (99%)
 Frame = +1

Query: 313  ALKLDQRGFRVLASCLTPSGAEDLQRVASSRLHTTLLDITDPQSVQQAAKWVEMHVKEAG 492
            AL+LDQRGFRVLASCLTPSGAEDLQRVASSRLHTTLLDITDPQSVQQAAKWVEMHVKEAG
Sbjct: 45   ALQLDQRGFRVLASCLTPSGAEDLQRVASSRLHTTLLDITDPQSVQQAAKWVEMHVKEAG 104

Query: 493  LFGLVNNAGVAGIIGPTPWLTRDDFQRVLNVNTMGPIGVTLALLPLLQQARGRVINITSV 672
            LFGLVNNAGVAGIIGPTPWLTRDDFQRVLNVNTMGPIGVTLALLPLLQQARGRVINITSV
Sbjct: 105  LFGLVNNAGVAGIIGPTPWLTRDDFQRVLNVNTMGPIGVTLALLPLLQQARGRVINITSV 164

Query: 673  LGRLAANGGGYCVSKFGLEAFSDSLRRDVAHFGIRVSIVEPGFFRTPVTNLESLEKTLQA 852
            LGRLAANGGGYCVSKFGLEAFSDSLRRDVAHFGIRVSIVEPGFFRTPVTNLESLEKTLQA
Sbjct: 165  LGRLAANGGGYCVSKFGLEAFSDSLRRDVAHFGIRVSIVEPGFFRTPVTNLESLEKTLQA 224

Query: 853  CWARLPPATQAHYGGAFLTKYLKMQQRIMNLICDPDLTKVSRCLEHALTARHPRTRYSPG 1032
            CWARLPPATQAHYGGAFLTKYLKMQQRIMNLICDPDLTKVSRCLEHALTARHPRTRYSPG
Sbjct: 225  CWARLPPATQAHYGGAFLTKYLKMQQRIMNLICDPDLTKVSRCLEHALTARHPRTRYSPG 284

Query: 1033 WDAKLLWLPASYLPASLVDAVLTWVLPKPAQAVY 1134
             WDAKLLWLPASYLPASLVDAVLTWVLPKPAQAVY
Sbjct: 285  WDAKLLWLPASYLPASLVDAVLTWVLPKPAQAVY 318 (SEQ ID NO:4)
```

Hmmer search results (Pfam):
Scores for sequence family classification (score includes all domains):
```
Model    Description                          Score      E-value   N
-------- -----------                          -----      -------   ---
PF00106  short chain dehydrogenase            137.5      4.1e-38   1
CE00062  CE00062 steroid_dehydrogenase       -178.0      0.015     1
```

Parsed for domains:
```
Model    Domain  seq-f  seq-t   hmm-f  hmm-t      score    E-value
-------- ------  -----  -----   -----  -----      -----    -------
PF00106   1/1      87    253 ..    17    203 .]    137.5   4.1e-38
CE00062   1/1      66    355 ..     1    337 []   -178.0   0.015
```

FIGURE 2B

```
   1 NNNNNNNNNN NNNNNNNNNN NNNATTCTAT TTAATTAGTC TGGAATCAAG
  51 GCTTTTTTTT TTTTTTTTTT GAGACAGAGT CCCACTCTGT CGCCCGGGCT
 101 GGAGTTCAGT GGCGTGATCT CGGCTCACTG CAACCTCTGC CTCCCAGGTT
 151 CAAGCGATTC TCCTGCCTCA GGCTCCTGAG TAGCTGGGAT TACAGGCTTG
 201 TGCCACTACG CCTGGCTAAA TTTTGTATTT TTAGTAGATA CAAGGTTTCA
 251 CCATGTTGGT CAGCCTGGTC TCGAACTCCT GACCTCGTGA TCCGCCCGCC
 301 TCGGCCTCCC AAAGTGCTGG GATTACGGGC GTGAGCCACC GCACCCGGCT
 351 AATCACGGCA TTTTTATAAG CCTTGTGATT TCTGTGATTC TAATGTTTAG
 401 ATTCTAATGC TTAGCCAGGG TTGAGAACCA CCGATTTAAT CCAATCCCTT
 451 CTCCTAGTTT TACTAAAGAG AAAACTATAA CCTAGAATGG TGAGCAACTT
 501 GCCCAAAGTC ACCCAACATG TTAGTGCAAG GTGCACCGAG AGAGATTGTA
 551 CCAGTAGCAA GAATATGCTC ATGATGTTTA TAATTGTTCT CGCTGGAGTT
 601 AATCCCGGAA GCATTTCTTT TTAGTTCACA GAGGCCTTAT ATAAATTACT
 651 TTTTACTTTG GCACAGCACT TACGCTTCTG CTAACACTGA AATGGGTTCG
 701 CATTCCTGAC CACAAAAGGA CAGAGATGAA ATTCTACATT CACACAGCCC
 751 GCCAAGTTAG CCAAGCTCCC TAGGAGGCTG TCTGAAGTGC CTAAAATGCT
 801 TCTCTACAAT GATCACCCAG AGCTGAGAGA CTTCAGTGGG GTAGTGAGAA
 851 GAAAGAGGGT TGGGAGAGAC AGGAAAGCAT CCTCTCCTTG AGGGAAGGAA
 901 CTGGGAATCA ACTGAGAACC AGCTAGCACT GCCAGGAGGT GAGGAGAGGG
 951 AAGGAGAATA ATTTAAATGA GGCCAGGGGA GCTTCTGCTC CCTCAATTAA
1001 ACGGTGATAG ACGGCCTGAC ACCACCAGCC CTCGAAGCCT GAGATCCACA
1051 GGAAATGTTA AAAACTGGCT TGGCAATATA AGTATTAGAA AATACTTCTT
1101 CCAACACTCA CCAAAAACTA AGCTCCCAAT AAAGAACACT TCACCTGCCC
1151 TCCGCAACCC TCTACCTCTC TTCCCCGCCA AGATCTTCAC CCAAGGTCTC
1201 AAGAGGGCGG TTCCCAACCT CACGTGACAC AGCGGTCACG TGACATGGCC
1251 CCGGGGAGCC GAGGTGAGCG TTCCAGCTTC CGGAGCCGGA GGGGGCCCGG
1301 CGTACCCAGC CCCCAGCCCG ACGTGACCAT GCTGTCCCGC CTCCTAAAAG
1351 AACACCAGGC CAAGCAGAAT GAACGCAAGG AGCTGCAGGG TGAGCCAAAT
1401 ATCCTGTCGG CCGTTTTCTC TTCGGCCGCG GCCTAGCTTC AGCCCGGAGC
1451 CTGGATCTCG AGTAACTAAC CATATCCAGG GAAAGACGCC AGCTAGCGGG
1501 CAACGGGCAT GGGGGNNNNN NNNNNNNNNN NNNNNNNNNN NNNNNNNNNN
1551 NNNNNNNNNN NNNNNNNNNN NNNNNNNNNN NNNNNNNNNN NNNNNNNNNN
1601 NNNNNNNNNN NNNNNNNNNN NNNNNNNNNN NNNNNNNNNN NNNNNNNNNN
1651 NNNNNNNNNN NNNNNNNNNN NNNNNNNNNN NNNNNNNNNN NNNNNNNNNN
1701 NNNNNNNNNN NNNNNNNNNN NNNNNNNNNN NNNNNNNNNN NNNNNNNNNN
1751 NNNNNNNNNN NNNNNNNNNN NNNNNNNNNN NNNNNNNNNN NNNNNNNNNN
1801 NNNNNNNNNN NNNNNNNNNN NNNNNNNNNN NNNNNNNNNN NNNNNNNNNN
1851 NNNNNNNNNN NNNNNNNNNN NNNNNNNNNN NNNNNNNNNN NNNNNNNNNN
1901 NNNNNNNNNN NNNNNNNNNN NNNNNNNNNN NNNNNNNNNN NNNNNNNNNN
1951 NNNNNNNNNN NNNNNNNNNN NNNNNNNNNN NNNNNNNNNN NNNNNNNNNN
2001 NNNNNNNNNN NNNNNNNNNN NNNNNNNNNN NNNNNNNNNN NNNNNNNNNN
2051 NNNNNNNNNN NNNNNNNNNN NNNNNNNNNN NNNNNNNNNN NNNNNNNNNN
2101 NNNNNNNNNN NNNNNNNNNN NNNNNNNNNN NNNNNNNNNN NNNNNNNNNN
2151 NNNNNNNNNN NNNNNNNNNN NNNNNNNNNN NNNNNNNNNN NNNNNNNNNN
2201 NNNNNNNNNN NNNNNNNNNN NNNNNNNNNN NNNNNNNNNN NNNNNNNNNN
2251 NNNNNNNNNN NNNNNNNNNN NNNNNNNNNN NNNNNNNNNN NNNNNNNNNN
2301 NNNNNNNNNN NNNNNNNNNN NNNNNNNNNN NNNNNNNNNN NNNNNNNNNN
2351 NNNNNNNNNN NNNNNNNNNN NNNNNNNNNN NNNNNNNNNN NNNNNNNNNN
2401 NNNNNNNNNN NNNNNNNNNN NNNNNNNNNN NNNNNNNNNN NNNNNNNNNN
2451 NNNNNNNNNN NNNNNNNNNN NNNNNNNNNN NNNNNNNNNN NNNNNNNNNN
2501 NNNNNNNNNN NNNNNNNNNN NNNNNNNNNN NNNNNNNNNN NNNNNNNNNN
2551 NNNNNNNNNN NNNNNNNNNN NNNNNNNNNN NNNNNNNNNN NNNNNNNNNN
2601 NNNNNNNNNN NNNNNNNNNN NNNNNNNNNN NNNNNNNNNN NNNNNNNNNN
2651 NNNNNNNNNN NNNNNNNNNN NNNNNNNNNN NNNNNNNNNN NNNNNNNNNN
```

FIGURE 3A

```
2701 NNNNNNNNNN NNNNNNNNNN NNNNNNNNNN NNNNNNNNNN NNNNNNNNNN
2751 NNNNNNNNNN NNNNNNNNNN NNNNNNNNNN NNNNNNNNNN NNNNNNNNNN
2801 NNNNNNNNNN NNNNNNNNNN NNNNNNNNNN NNNNNNNNNN NNNNNNNNNN
2851 NNNNNNNNNN NNNNNNNNNN NNNNNNNNNN NNNNNNNNNN NNNNNNNNNN
2901 NNNNNNNNNN NNNNNNNNNN NNNNNNNNNN NNNNNNNNNN NNNNNNNNNN
2951 NNNNNNNNNN NNNNNNNNNN NNNNNNNNNN NNNNNNNNNN NNNNNNNNNN
3001 NNNNNNNNNN NNNNNNNNNN NNNNNNNNNN NNNNNNNNNN NNNNNNNNNN
3051 NNNNNNNNNN NNNNNNNNNN NNNNNNNNNN NNNNNNNNNN NNNNNNNNNN
3101 NNNNNNNNNN NNNNNNNNNN NNNNNNNNNN NNNNNNNNNN NNNNNNNNNN
3151 NNNNNNNNNN NNNNNNNNNN NNNNNNNNNN NNNNNNNNNN NNNNNNNNNN
3201 NNNNNNNNNN NNNNNNNNNN NNNNNNNNNN NNNNNNNNNN NNNNNNNNNN
3251 NNNNNNNNNN NNNNNNNNNN NNNNNNNNNN NNNNNNNNNN NNNNNNNNNN
3301 NNNNNNNNNN NNNNNNNNNN NNNNNNNNNN NNNNNNNNNN NNNNNNNNNN
3351 NNNNNNNNNN NNNNNNNNNN NNNNNNNNNN NNNNNNNNNN NNNNNNNNNN
3401 NNNNNNNNNN NNNNNNNNNN NNNNNNNNNN NNNNNNNNNN NNNNNNNNNN
3451 NNNNNNNNNN NNNNNNNNNN NNNNNNNNNN NNNNNNNNNN NNNNNNNNNN
3501 NNNNNNNNNN NNTCCCCTCC AATTCCTTTT CCCCCTCTCC CCAGCAAAAT
3551 AGGAGGCGAG AGGCTATCAC TGCAGCGACC TGCCTGACAG AAGCTTTGGT
3601 GGATCACCTC AATGTGGGGT ATGGACCTCT TATCAACATC AGTTTCCTCC
3651 TTCCCCACCC CGCCCAAGTT TAGGCACTGG CCAGTCTGGC CCTCAAATAG
3701 CTGTTGAAGG GGTGGGATGT TCCACTAATT CCCCTATCCT ACCCCGCCCC
3751 TCCCAGCTCT TTGTAGAGCA ACTTGAGTCA ACTCTGAGTC CTAGCACTGG
3801 GCAAGGGAGG AACAGCTGCC GTGGTTAGAG AAGCAGCCAG ATTTCCCCTT
3851 CCCCACGTTA ACTTCCCTGG CATTTACAAC TTGATGCCAT CTGCCCACCT
3901 CCCTTCACCC TTCCAAGTCC AGCTGTCACT TCAGCAGGAG GGAGAGCACC
3951 CTCCTTCATT ACAGCTTACC ACCCTCTCCT CTGCCTCCCA CCCTCTGGCA
4001 AGCCTGGGGA GCAGCTGGCA GGAAAGAGAT GGCAGAGCTG GTGGTGGTGA
4051 GAGTAGAACC TGTTCCGGGA GCTATGGCAG AGCCAGGCTG TCTCTTACCT
4101 TCCTATTGGG TCTCTAGGGA CCACACCCTG CCCCAGCCCT AAATGAGAAT
4151 GCAAGTAACA GCCAAAGACT TGGGAAAAAG CAAAGAACAT TGTCTCTTGA
4201 CCCTAAGTGA CCCAGAAGCG TGCAGAGATG ATGATTTGCT AGTCTGCCTA
4251 TTGGAAGAAA GGCAGTATGG TACCTTCCAC CCCAGGTCAA GTAGAACAGC
4301 TCGGTGTGAA TCCAGAGACT GAGTCATCCA AGTGAGCCAT GCAGGGGCTG
4351 GGGTCATCTT TGTTACTCAT CTTGGGGGAA GGTTGAGAGA AAGAAAGTTG
4401 TGGCTGGGGC CTCTGATCTC CCTTCTCTCC AGGCAGCTCT CTTTACTCAG
4451 TGTGAATATA GAAGCAGGTG GTCAATGGGG AAAACCAGAA GTTCAGGAAT
4501 TCTCAGGGGA GTCTGTTTCA GTTCCTACCC GACCCTTGAC AGTGACCCAG
4551 CTGTCTCCCA AAAAGAAGGA ACAGGGTCTG CCCTCCCATT TCCTCCCTCC
4601 CACATTGGCA CCTCCTGGGC TCTGCTGTGC CCATCATTTG TGAGATTGGC
4651 CCAGGCCTTT CCCTCTTCTT TTCCTTTGCT AGATGCCACC CCACTTTCAG
4701 CTTAGAGGGC AGCTAAGCCA AAGCCAGATT AGAAAGGGTT TTGTGTTGCT
4751 GCCCACGCCT CCTCTCATTC CCCGGAAAGG AAAACAAAGG CTCAGTCTAT
4801 CTTGGCCCCT GTCAGGTGTC CTGCCCACTC CCTCAGCCCC CACCAACCCC
4851 TTCCCCGCTC CAGCCCCCAC ACATTCCAGT GGGTGGGGGC ACCGGATGTG
4901 GAATCTCCTG GCTGAGTAGA GCTCTGGGGT GGGAAGTGAA AAATTCAACA
4951 GCCAATAAAG GAGAACAATT ATTGCAGGGG TTGGGGAGGG CAAAAAACAC
5001 TGGCAGAAGG TTGGGGACAC CAACCCCATG GTAGTAATGG TAACCACAGC
5051 CCATACCTTG ATTGAAAAGA AAAACTAGTG CCTAAGGCAG AAGGGAGGGA
5101 GAGCATGTGT GTGTGTGTGT GTGTGTGTTT GTGTGTGTTC CTTGATCTGT
5151 GTGGGCAAAA GCGAAGGCTT GGGAGAGCAA CTGAGAGCCG AGAAGAAACC
5201 CCTGGGATAC CCTCTTTTGA CCCAGGGTTC CTGGGGAGGG GGTTTGTACT
5251 CCCATCCTAA CCCGGCTTCA GGGAGGGGCC CAATTTCCCT CTCCAACTTC
5301 TTGCATAGAT CCCTAGGCTT CCAATCACTG CCAGATGTGT TCCTCCTGCT
5351 GGNNNNNNNN NNNNNNNNNN NNNNNNNNNN NNNNNNNNNN NNNNNNNNNN
```

FIGURE 3B

```
5401  NNNNNNNNNN NNNNNNNNNN NNNNNNNNNN NNNNNNNNNN NNNNNNNNNN
5451  NNNNNNNNNC CAGGTTTTCC CTCCCTTCCC CCACTCAGCT GCAGGAACTC
5501  CTTTTTGGGG TTTGGAGCTG GTATGTTTCT AGTCAGCTCC GAGCTTGGCT
5551  CTCCTGGGAA TCCTGGGAGT GAAAGGAAGG AGCTGGGTTT ATTTGCATGT
5601  ACTGGTAGTC ATTTGCATCA CATCCAAAAA TGGCCAAAAT TATGAGCCCT
5651  GATTCTTGGC TGAACTCCCA CTGCTGCAAT GGAATATTAG TCCCGGAGAC
5701  CACCCCCAAC TAGCTGGAGC TGATCTCCTC CCTCCTCCAA CCCCCCAGTG
5751  TGGCCCAGGC CTACATGAAC CAGAGAAAGC TGGACCATGA GGTGAAGACC
5801  CTACAGGTCC AGGCTGCCCA ATTTGCCAAG CAGACAGGCC AGTGGATCGG
5851  AATGGTGGAG AACTTCAACC AGGCACTCAA GGTGGGCCAT ACTCCCTACC
5901  TCACCACCCC AATCCTGGGC CCCCATTGGC TGCCTCCAGT CAGGTTACCT
5951  CAGGTTTAGG TTAAGGAGGA AGTAGGGTGG TCCCAGAAAC CCCATCTATA
6001  GCCCCAGTGT CAGAAAAGGT AGAGAAAGAA AGAAAAGCAG TTGGTGGGTC
6051  CAAGTAAAGC CTTTTCCAGG AGATGAATAA AACGTATTCC CCAGACTGGA
6101  AGCCATACTC TACCCATTCT GATTCCTGGG CTCCCACCTC CTCTCCCCCT
6151  TCCCAGGAAA TTGGGGATGT GGAGAACTGG GCTCGGAGCA TCGAGCTGGA
6201  CATGCGCACC ATTGCCACTG CACTGGAATA TGTCTACAAA GGGCAGCTGC
6251  AGTCTGCCCC TTCCTAGCCC CTGTTCCCTC CCCCAACCCT ATCCCTCCTA
6301  CCTCACCCGC AGGGGGAAGG AGGGAGGCTG ACAAGCCTTG AATAAAACAC
6351  AAGCCTCCGT TTCTCTGTGG TGTGTTTCAG AGAGCTACTA GCTCCAGTGT
6401  CGGGGGTGGG AGTGGAAGGT TCAAAGGTGG TTTCCCTGAG GGACAGGTAC
6451  CTTTTGGGGA GAGGGTGGAA CTAGCTTCCT CTTACTATCC CAACTCTCTT
6501  CTCCTCCATG GCCCTTGTGC AGGTGTCTGT TAGGCAAGCA GAGGGTGGGA
6551  GTTCCCATCC CTCCTGAGAG AAGGTCCTAG TAGCCCTGCC CCAAGCTTCC
6601  TAATTCAGGA CTTGTTTCCT ACAGAAGAGA AACAAGGCAA GGTACAGGCC
6651  TGGTCCCCAG CTCTGGCTTT CTGCCTCTCC ACGTGCTCAT GGCCTCTCCC
6701  AGGCTAACTC TAAGCAGTGT CATGAGTCTG AGCCAGGTGG GAGATTAATT
6751  CCTGGGGGCA CTTCAGGGCT GAGAAGGGGG AGGAATGACA GGTCCAGTAA
6801  CCGTTACCAA CAGAGCAGTG CAGCTGCCAT CCTTGACAGC TCCCTCCTCC
6851  TTGGAGACCA TGACATAGAT GGTCAGGAAC CCAGGCTGAG AAAGACAGCC
6901  AAGGGGTGGG GGGAGCCTAG GCAAATCTGG CCTCTGCCAA GTCCTGGCTT
6951  CAGCCAGGCA AGCTCCAGCC TCCCTGGCTC CTCCTCCTCC TCAGTCCTAT
7001  CCCCACCCTG TCACACATAC ACTTAATACG CCTGGCATCC AAGTCCACCC
7051  ACTCCGGACT TTGGCCTTAG CAGTAGTTAG TGTGGGAGGC TGGGAAGACT
7101  GGGAGCAGTC TCTTAAACAA AAGCAAAAGA ATAAGCTTCG GGCGCTGTAG
7151  TACCTGCCAG CTTTCGCCAC AGGAGGTAAG TGGATACTGG GAGCTGGGGG
7201  AACTGAGAAG ACTAGCCAGA TATTACATGT ATTGCCAACT CAAAACTTTC
7251  AGCTTTTAAC ATGCTTCCTC ACACATTATC CCCTTTGATC CTCCACAACT
7301  CTGAGGTGGA CCTGGTGGGT CTTAGCCCCA CTTGGTAGAT GAGAAAATAG
7351  GTTGAGAGAG ACAGTGAGAT GCTCAGTATC ACACAGCAAA CCTCTTGGCC
7401  CTATACATCA TTCCAAACAC AAGACCCAGG TTGCATATAG AAGGTTCAGT
7451  GTCCCTGGTT TAGAAGGAGA GGTGGTGTGA GGCAAGCAAG AAGATGCCTC
7501  TGCTGCACTC CAGCCTGGGC GACAGAGTGA GACTCCATCT CAAAAAAAAA
7551  AAAAAAAAAA AAAAGATGCC TCTGCTCCAT ACAGCAGGTC TGTACACAGG
7601  ATCTGGCTCA TGTGGTTTTA GTTNNNNNNN NNNNNNNNNN NNNNNNNNNN
7651  NNNNNNNNNN NNNNNNNNNN NNNNNNNNNN NNNNNNNNNN NNNNNNNNNN
7701  TGGTTTTAGT TAAAGTTAGC CACAAATACA GCGTCTGCCC ACATCTTTGC
7751  TTTGAACAGA TGAGCCATGG TTGGCCAATT ATCTGCCAAC CAGATAATTT
7801  CTCAATATGC TCACACCAGA TGCTTCCAGC TAGGGAGGGT ATTAGGGGAA
7851  AGGGCTTGAG GGCCACAGTA AACTGGACAA GTTTTTCTGC CCAGCCTAGG
7901  CTGCCACCTG TAGGTCACTT GGGCTCCAGC TATGTGGCTG CCTCTTCTGC
7951  TGGGTGCCTT ACTCTGGGCA GTGCTGTGGT TGCTCAGGGA CCGGCAGAGC
8001  CTGCCCGCCA GCAATGCCTT TGTCTTCATC ACCGGCTGTG ACTCAGGCTT
8051  TGGGCGCCTT CTGGCACTGC AGCTGGACCA GAGAGGCTTC CGAGTCCTGG
```

FIGURE 3C

```
8101  CCAGCTGCCT GACCCCCTCC GGGGCCGAGG ACCTGCAGCG GGTGGCCTCC
8151  TCCCGCCTCC ACACCACCCT GTTGGATATC ACTGATCCCC AGAGCGTCCA
8201  GCAGGCAGCC AAGTGGGTGG AGATGCACGT TAAGGAAGCA GGTAAGTATG
8251  GTAGACCACC AGGAATATGG TGTGGGGTGT CCTGATCCCC ACAGTCACCC
8301  CAGGAGTCAC CTGCAAGGGC TGTGGTAAGC TAAAGGGACA ATTTGAGGAG
8351  AAGCAGTTTT CAGATGCTCC CAGGAAGAAG AGGGAGCTGT GGGAGTGCCT
8401  CACCTACCCC CAGCATCCTT TTCATCTCCC CACAGGGCTT TTTGGTCTGG
8451  TGAATAATGC TGGTGTGGCT GGTATCATCG GACCCACACC ATGGCTGACC
8501  CGGGACGATT TCCAGCGGGT GCTGAATGTG AACACAATGG GTCCCATTGG
8551  GGTCACCCTT GCCCTGCTGC CTCTGCTGCA GCAAGCCCGG GGCCGGGTGA
8601  TCAACATCAC CAGCGTCCTG GGTCGCCTGG CAGCCAATGG TGGGGGCTAC
8651  TGTGTCTCCA AATTTGGCCT GGAGGCCTTC TCTGACAGCC TGAGGTGAGG
8701  GGTACAGGGC TCTGGGTTCC AGGACTAACA GCAGCCCACT CAACAAACGT
8751  GGGCCAGCAG AGGTGGTTAA AATACAGCAC ATTGGAATAG TTAAAAAGAG
8801  ACAGTTTAGG GCTAAACTTC ATGGGTTCAA TGAAGTCTAC CCTTATGTAA
8851  GCTTTGTGAC NNNNNNNNNN NNNNNNNNNN NNNNNNNNNN NNNNNNNNNN
8901  NNNNNNNNNN NNNNNNNNNN NNNNNNNNNN NNNNNNNNNN NNNNNNNNNN
8951  NNNNNNNNNN NNNNNNNNNN NNNNNNNNNN NNNNNNNNNN NNNNNNNNNN
9001  NNNNNNNNNN NNNNNNNNNN NNNNNNNNNN NNNNNNNNNN NNNNNNNNNN
9051  NNNNNNNNNN NNNNNNNNNN NNNNNNNNNN NNNNNNNNNN NNNNNNNNNN
9101  NNNNNNNNNN NNNNNNNNNN NNNNNNNNNN NNNNNNNNNN NNNNNNNNNN
9151  NNNNNNNNNN NNNNNNNNNN NNNNNNNNNN NNNNNNNNNN NNNNNNNNNN
9201  NNNNNNNNNN NNNNNNNNNN NNNNNNNNNN NNNNNNNNNN NNNNNNNNNN
9251  NNNNNNNNNN NNNNNNNNNN NNNNNNNNNN NNNNNNNNNN NNNNNNNNNN
9301  NNNNNNNNNN NNNNNNNNNN NNNNNNNNNN NNNNNNNNNN NNNNNNNNNN
9351  NNNNNNNNNN NNNNNNNNNN NNNNNNNNNN NNNNNNNNNN NNNNNNNNNN
9401  NNNNNNNNNN NNNNNNNNNN NNNNNNNNNN NNNNNNNNNN NNNNNNNNNN
9451  NNNNNNNNNN NNNNNNNNNN NNNNNNNNNN NNNNNNNNNN NNNNNNNNNN
9501  NNNNNNNNNN NNNNNNNNNN NNNNNNNNNN NNNNNNNNNN NNNNNNNNNN
9551  NNNNNNNNNN NNNNNNNNNN NNNNNNNNNN NNNNNNNNNN NNNNNNNNNN
9601  NNNNNNNNNN NNNNNNNNNN NNNNNNNNNN NNNNNNNNNN NNNNNNNNNN
9651  NNNNNNNNNN NNNNNNNNNN NNNNNNNNNN NNNNNNNNNN NNNNNNNNNN
9701  NNNNNNNNNN NNNNNNNNNN NNNNNNNNNN NNNNNNNNNN NNNNNNNNNN
9751  NNNNNNNNNN NNNNNNNNNN NNNNNNNNNN NNNNNNNNNN NNNNNNNNNN
9801  NNNNNNNNNN NNNNNNNNNN NNNNNNNNNN NNNNNNNNNN NNNNNNNNNN
9851  NNNNNNNNNN NNNNNNNNNN NNNNNNNNNN NNNNNNNNNN NNNNNNNNNN
9901  NNNNNNNNNN NNNNNNNNNN NNNNNNNNNN NNNNNNNNNN NNNNNNNNNN
9951  NNNNNNNNNN NNNNNNNNNN NNNNNNNNNN NNNNNNNNNN NNNNNNNNNN
10001 NNNNNNNNNN NNNNNNNNNN NNNNNNNNNN NNNNNNNNNN NNNNNNNNNN
10051 NNNNNNNNNN NNNNNNNNNN NNNNNNNNNN NNNNNNNNNN NNNNNNNNNN
10101 NNNNNNNNNN NNNNNNNNNN NNNNNNNNNN NNNNNNNNNN NNNNNNNNNN
10151 NNNNNNNNNN NNNNNNNNNN NNNNNNNNNN NNNNNNNNNN NNNNNNNNNN
10201 NNNNNNNNNN NNNNNNNNNN NNNNNNNNNN NNNNNNNNNN NNNNNNNNNN
10251 NNNNNNNNNN NNNNNNNNNN NNNNNNNNNN NNNNNNNNNN NNNNNNNNNN
10301 NNNNNNNNNN NNNNNNNNNN NNNNNNNNNN NNNNNNNNNN NNNNNNNNNN
10351 NNNNNNNNNN NNNNNNNNNN NNNNNNNNNN NNNNNNNNNN NNNNNNNNNN
10401 NNNNNNNNNN NNNNNNNNNN NNNNNNNNNN NNNNNNNNNN NNNNNNNNNN
10451 NNNNNNNNNN NNNNNNNNNN NNNNNNNNNN NNNNNNNNNN NNNNNNNNNN
10501 NNNNNNNNNN NNNNNNNNNN NNNNNNNNNN NNNNNNNNNN NNNNNNNNNN
10551 NNNNNNNNNN NNNNNNNNNN NNNNNNNNNN NNNNNNNNNN NNNNNNNNNN
10601 NNNNNNNNNN NNNNNNNNNN NNNNNNNNNN NNNNNNNNNN NNNNNNNNNN
10651 NNNNNNNNNN NNNNNNNNNN NNNNNNNNNN NNNNNNNNNN NNNNNNNNNN
10701 NNNNNNNNNN NNNNNNNNNN NNNNNNNNNN NNNNNNNNNN NNNNNNNNNN
10751 NNNNNNNNNN NNNNNNNNNN NNNNNNNNNN NNNNNNNNNN NNNNNNNNNN
```

FIGURE 3D

| | | | | | |
|---|---|---|---|---|---|
| 10801 | NNNNNNNNNN | NNNNNNNNNN | NNNNNNNNNN | NNNNNNNNNN | NNNNNNNNNN |
| 10851 | NNNNNNNNNN | NNNNNNNNNN | NNNNNNNNNN | NNNNNNNNNN | NNNNNNNNNN |
| 10901 | NNNNNNNNNN | NNNNNNNNNN | NNNNNNNNNN | NNNNNNNNNN | NNNNNNNNNN |
| 10951 | NNNNNNNNNN | NNNNNNNNNN | NNNNNNNNNN | NNNNNNNNNN | NNNNNNNNNN |
| 11001 | NNNNNNNNNN | NNNNNNNNNN | NNNNNNNNNN | NNNNNNNNNN | NNNNNNNNNN |
| 11051 | NNNNNNNNNN | NNNNNNNNNN | NNNNNNNNNN | NNNNNNNNNN | NNNNNNNNNN |
| 11101 | NNNNNNNNNN | NNNNNNNNNN | NNNNNNNNNN | NNNNNNNNNN | NNNNNNNNNN |
| 11151 | NNNNNNNNNN | NNNNNNNNNN | NNNNNNNNNN | NNNNNNNNNN | NNNNNNNNNN |
| 11201 | NNNNNNNNNN | NNNNNNNNNN | NNNNNNNNNN | NNNNNNNNNN | NNNNNNNNNN |
| 11251 | NNNNNNNNNN | NNNNNNNNNN | NNNNNNNNNN | NNNNNNNNNN | NNNNNNNNNN |
| 11301 | NNNNNNNNNN | NNNNNNNNNN | NNNNNNNNNN | NNNNNNNNNN | NNNNNNNNNN |
| 11351 | NNNNNNNNNN | NNNNNNNNNN | NNNNNNNNNN | NNNNNNNNNN | NNNNNNNNNN |
| 11401 | NNNNNNNNNN | NNNNNNNNNN | NNNNNNNNNN | NNNNNNNNNN | NNNNNNNNNN |
| 11451 | NNNNNNNNNN | NNNNNNNNNN | NNNNNNNNNN | NNNNNNNNNN | NNNNNNNNNN |
| 11501 | NNNNNNNNNN | NNNNNNNNNN | NNNNNNNNNN | NNNNNNNNNN | NNNNNNNNNN |
| 11551 | NNNNNNNNNN | NNNNNNNNNN | NNNNNNNNNN | NNNNNNNNNN | NNNNNNNNNN |
| 11601 | NNNNNNNNNN | NNNNNNNNNN | NNNNNNNNNN | NNNNNNNNNN | NNNNNNNNNN |
| 11651 | NNNNNNNNNN | NNNNNNNNNN | NNNNNNNNNN | NNNNNNNNNN | NNNNNNNNNN |
| 11701 | NNNNNNNNNN | NNNNNNNNNN | NNNNNNNNNN | NNNNNNNNNN | NNNNNNNNNN |
| 11751 | NNNNNNNNNN | NNNNNNNNNN | NNNNNNNNNN | NNNNNNNNNN | NNNNNNNNNN |
| 11801 | NNNNNNNNNN | NNNNNNNNNN | NNNNNNNNNN | NNNNNNNNNN | NNNNNNNNNN |
| 11851 | NNNNNNNNNN | NNNNNNNNNN | NNNNNNNNNN | NNNNNNNNNN | NNNNNNNNNN |
| 11901 | NNNNNNNNNN | NNNNNNNNNN | NNNNNNNNNN | NNNNNNNNNN | NNNNNNNNNN |
| 11951 | NNNNNNNNNN | NNNNNNNNNN | NNNNNNNNNN | NNNNNNNNNN | NNNNNNNNNN |
| 12001 | NNNNNNNNNN | NNNNNNNNNN | NNNNNNNNNN | NNNNNNNNNN | NNNNNNNNNN |
| 12051 | NNNNNNNNNN | NNNNNNNNNN | NNNNNNNNNN | NNNNNNNNNN | NNNNNNNNNN |
| 12101 | NNNNNNNNNN | NNNNNNNNNN | NNNNNNNNNN | NNNNNNNNNN | NNNNNNNNNN |
| 12151 | NNNNNNNNNN | NNNNNNNNNN | NNNNNNNNNN | NNNNNNNNNN | NNNNNNNNNN |
| 12201 | NNNNNNNNNN | NNNNNNNNNN | NNNNNNNNNN | NNNNNNNNNN | NNNNNNNNNN |
| 12251 | NNNNNNNNNN | NNNNNNNNNN | NNNNNNNNNN | NNNNNNNNNN | NNNNNNNNNN |
| 12301 | NNNNNNNNNN | NNNNNNNNNN | NNNNNNNNNN | NNNNNNNNNN | NNNNNNNNNN |
| 12351 | NNNNNNNNNN | NNNNNNNNNN | NNNNNNNNNN | NNNNNNNNNN | NNNNNNNNNN |
| 12401 | NNNNNNNNNN | NNNNNNNNNN | NNNNNNNNNN | NNNNNNNNNN | NNNNNNNNNN |
| 12451 | NNNNNNNNNN | NNNNNNNNNN | NNNNNNNNNN | NNNNNNNNNN | NNNNNNNNNN |
| 12501 | NNNNNNNNNN | NNNNNNNNNN | NNNNNNNNNN | NNNNNNNNNN | NNNNNNNNNN |
| 12551 | NNNNNNNNNN | NNNNNNNNNN | NNNNNNNNNN | NNNNNNNNNN | NNNNNNNNNN |
| 12601 | NNNNNNNNNN | NNNNNNNNNN | NNNNNNNNNN | NNNNNNNNNN | NNNNNNNNNN |
| 12651 | NNNNNNNNNN | NNNNNNNNNN | NNNNNNNNNN | NNNNNNNNNN | NNNNNNNNNN |
| 12701 | NNNNNNNNNN | NNNNNNNNNN | NNNNNNNNNN | NNNNNNNNNN | NNNNNNNNNN |
| 12751 | NNNNNNNNNN | NNNNNNNNNN | NNNNNNNNNN | NNNNNNNNNN | NNNNNNNNNN |
| 12801 | NNNNNNNNNN | NNNNNNNNNN | NNNNNNNNNN | NNNNNNNNNN | NNNNNNNNNN |
| 12851 | NNNNNNNNNN | NNNNNNNNNN | NNNNNNNNNN | NNNNNNNNNN | NNNNNNNNNN |
| 12901 | NNNNNNNNNN | NNNNNNNNNN | NNNNNNNNNN | NNNNNNNNNN | NNNNNNNNNN |
| 12951 | NNNNNNNNNN | NNNNNNNNNN | NNNNNNNNNN | NNNNNNNNNN | NNNNNNNNNN |
| 13001 | NNNNNNNNNN | NNNNNNNNNN | NNNNNNNNNN | NNNNNNNNNN | NNNNNNNNNN |
| 13051 | NNNNNNNNNN | NNNNNNNNNN | NNNNNNNNNN | NNNNNNNNNN | NNNNNNNNNN |
| 13101 | NNNNNNNNNN | NNNNNNNNNN | NNNNNNNNNN | NNNNNNNNNN | NNNNNNNNNN |
| 13151 | NNNNNNNNNN | NNNNNNNNNN | NNNNNNNNNN | NNNNNNNNNN | NNNNNNNNNN |
| 13201 | NNNNNNNNNN | NNNNNNNNNN | NNNNNNNNNN | NNNNNNNNNN | NNNNNNNNNN |
| 13251 | NNNNNNNNNN | NNNNNNNNNN | NNNNNNNNNN | NNNNNNNNNN | NNNNNNNNNN |
| 13301 | NNNNNNNNNN | NNNNNNNNNN | NNNNNNNNNN | NNNNNNNNNN | NNNNNNNNNN |
| 13351 | NNNNNNNNNN | NNNNNNNNNN | NNNNNNNNNN | NNNNNNNNNN | NNNNNNNNNN |
| 13401 | NNNNNNNNNN | NNNNNNNNNN | NNNNNNNNNN | NNNNNNNNNN | NNNNNNNNNN |
| 13451 | NNNNNNNNNN | NNNNNNNNNN | NNNNNNNNNN | NNNNNNNNNN | NNNNNNNNNN |

FIGURE 3E

```
13501  NNNNNNNNNN NNNNNNNNNN NNNNNNNNNN NNNNNNNNNN NNNNNNNNNN
13551  NNNNNNNNNN NNNNNNNNNN NNNNNNNNNN NNNNNNNNNN NNNNNNNNNN
13601  NNNNNNNNNN NNNNNNNNNN NNNNNNNNNN NNNNNNNNNN NNNNNNNNNN
13651  NNNNNNNNNN NNNNNNNNNN NNNNNNNNNN NNNNNNNNNN NNNNNNNNNN
13701  NNNNNNNNNN NNNNNNNNNN NNNNNNNNNN NNNNNNNNNN NNNNNNNNNN
13751  NNNNNNNNNN NNNNNNNNNN NNNNNNNNNN NNNNNNNNNN NNNNNNNNNN
13801  NNNNNNNNNN NNNNNNNNNN NNNNNNNNNN NNNNNNNNNN NNNNNNNNNN
13851  NNNNNNNNNN NNNNNNNNNN NNNNNNNNNN NNNNNNNNNN NNNNNNNNNN
13901  NNNNNNNNNN NNNNNNNNNN NNNNNNNNNN NNNNNNNNNN NNNNNNNNNN
13951  NNNNNNNNNN NNNNNNNNNN NNNNNNNNNN NNNNNNNNNN NNNNNNNNNN
14001  NNNNNNNNNN NNNNNNNNNN NNNNNNNNNN NNNNNNNNNN NNNNNNNNNN
14051  NNNNNNNNNN NNNNNNNNNN NNNNNNNNNN NNNNNNNNNN NNNNNNNNNN
14101  NNNNNNNNNN NNNNNNNNNN NNNNNNNNNN NNNNNNNNNN NNNNNNNNNN
14151  NNNNNNNNNN NNNNNNNNNN NNNNNNNNNN NNNNNNNNNN NNNNNNNNNN
14201  NNNNNNNNNN NNNNNNNNNN NNNNNNNNNN NNNNNNNNNN NNNNNNNNNN
14251  NNNNNNNNNN NNNNNNNNNN NNNNNNNNNN NNNNNNNNNN NNNNNNNNNN
14301  NNNNNNNNNN NNNNNNNNNN NNNNNNNNNN NNNNNNNNNN NNNNNNNNNN
14351  NNNNNNNNNN NNNNNNNNNN NNNNNNNNNN NNNNNNNNNN NNNNNNNNNN
14401  NNNNNNNNNN NNNNNNNNNN NNNNNNNNNN NNNNNNNNNN NNNNNNNNNN
14451  NNNNNNNNNN NNNNNNNNNN NNNNNNNNNN NNNNNNNNNN NNNNNNNNNN
14501  NNNNNNNNNN NNNNNNNNNN NNNNNNNNNN NNNNNNNNNN NNNNNNNNNN
14551  NNNNNNNNNN NNNNNNNNNN NNNNNNNNNN NNNNNNNNNN NNNNNNNNNN
14601  NNNNNNNNNN NNNNNNNNNN NNNNNNNNNN NNNNNNNNNN NNNNNNNNNN
14651  NNNNNNNNNN NNNNNNNNNN NNNNNNNNNN NNNNNNNNNN NNNNNNNNNN
14701  NNNNNNNNNN NNNNNNNNNN NNNNNNNNNN NNNNNNNNNN NNNNNNNNNN
14751  NNNNNNNNNN NNNNNNNNNN NNNNNNNNNN NNNNNNNNNN NNNNNNNNNN
14801  NNNNNNNNNN NNNNNNNNNN NNNNNNNNNN NNNNNNNNNN NNNNNNNNNN
14851  NNNNNNNNNN NNNNNNNNNN NNNNNNNNNN NNNNNNNNNN NNNNNNNNNN
14901  NNNNNNNNNN NNNNNNNNNN NNNNNNNNNN NNNNNNNNNN NNNNNNNNNN
14951  NNNNNNNNNN NNNNNNNNNN NNNNNNNNNN NNNNNNNNNN NNNNNNNNNN
15001  NNNNNNNNNN NNNNNNNNNN NNNNNNNNNN NNNNNNNNNN NNNNNNNNNN
15051  NNNNNNNNNN NNNNNNNNNN NNNNNNNNNN NNNNNNNNNN NNNNNNNNNN
15101  NNNNNNNNNN NNNNNNNNNN NNNNNNNNNN NNNNNNNNNN NNNNNNNNNN
15151  NNNNNNNNNN NNNNNNNNNN NNNNNNNNNN NNNNNNNNNN NNNNNNNNNN
15201  NNNNNNNNNN NNNNNNNNNN NNNNNNNNNN NNNNNNNNNN NNNNNNNNNN
15251  NNNNNNNNNN NNNNNNNNNN NNNNNNNNNN NNNNNNNNNN NNNNNNNNNN
15301  NNNNNNNNNN NNNNNNNNNN NNNNNNNNNN NNNNNNNNNN NNNNNNNNNN
15351  NNNNNNNNNN NNNNNNNNNN NNNNNNNNNN NNNNNNNNNN NNNNNNNNNN
15401  NNNNNNNNNN NNNNNNNNNN NNNNNNNNNN NNNNNNNNNN NNNNNNNNNN
15451  NNNNNNNNNN NNNNNNNNNN NNNNNNNNNN NNNNNNNNNN NNNNNNNNNN
15501  NNNNNNNNNN NNNNNNNNNN NNNNNNNNNN NNNNNNNNNN NNNNNNNNNN
15551  NNNNNNNNNN NNNNNNNNNN NNNNNNNNNN NNNNNNNNNN NNNNNNNNNN
15601  NNNNNNNNNN NNNNNNNNNN NNNNNNNNNN NNNNNNNNNN NNNNNNNNNN
15651  NNNNNNNNNN NNNNNNNNNN NNNNNNNNNN NNNNNNNNNN NNNNNNNNNN
15701  NNNNNNNNNN NNNNNNNNNN NNNNNNNNNN NNNNNNNNNN NNNNNNNNNN
15751  NNNNNNNNNN NNNNNNNNNN NNNNNNNNNN NNNNNNNNNN NNNNNNNNNN
15801  NNNNNNNNNN NNNNNNNNNN NNNNNNNNNN NNNNNNNNNN NNNNNNNNNN
15851  NNNNNNNNNN NNNNNNNNNN NNNNNNNNNN NNNNNNNNNN NNNNNNNNNN
15901  NNNNNNNNNN NNNNNNNNNN NNNNNNNNNN NNNNNNNNNN NNNNNNNNNN
15951  NNNNNNNNNN NNNNNNNNNN NNNNNNNNNN NNNNNNNNNN TTCTTAGCAG
16001  GAGTATAAGG CGCCTAAGCT TAGTCTACCT TTTAAGGAAG CCTGCGTTTG
16051  TCACCATCAC TCAGCAAATA ACCTGAATGT CTCCTGTCTC TCAGCCTTAA
16101  TTTTTCAGGC AGCATCATGG GACACATACT TTTAGTTTTG AGACAAGGCC
16151  TTGCTCTCAC CCAGGGTGGA GTGCAGTGGT GCAGTCACGG CCCACTGAAC
```

FIGURE 3F

```
16201  TTCAAACTCC TAGGCTCAAG CAGCTCAAGC GATATCCGCC TCAGCCTCCT
16251  GAGTAGCTGA GACCACAGGC GCGTGCCAGC ATGCCTGGCT AGTATTTTTT
16301  TACAGATGGG GTCTTGCTGT GGTGACCAGA CTTGTCTCAA ACTCCCGGCC
16351  TCAAGCGATG CTTCCGCCTG GGCCTCCCAA AGTGTTGGGA TTATAGGTGT
16401  GAGCCACTGC ATACTGGAAC ACATACTTTA TACTTGAATT TTTTTTTATC
16451  CCCTTCCCTC CTGCTCCTTA CCTATACTTG GATTTCTACA TCTGTGCCAG
16501  GGCAGTGGGA TGTATCCCCA CTTTCCCCAT CAGCTTACCC TCCAGCAAAT
16551  ACGAGACTAT ACCCTTCAAT ATCCAGCACT CAGGGCTCAA CCATGTGTTT
16601  TGGGAGCAAG GGAATGGGGT TCCTCTAGGT CAGGAATCGG CAAACTCAGT
16651  ACTCAAGCCA GATCTGGCCA GCTGCCTACA AGCTGATAAT GGTTTTTTTT
16701  ATTTTTAAAT GGTTACATTG TAAACTGTTA TATAAGTACC TGATAATATC
16751  ATTAATTTTG TTTCTTGGCC TGCCATGCTT AAAATATTAA CTCTCTGGCC
16801  CTTTAAGAAA AAAACGTGCT GACCCCTGCT CTAGATCAAA GAAAACAAAC
16851  CTCAAAAATA CTTTCCTCCC TCTACCCCAC TTGACCCTTG TCCCGGGGCA
16901  GTAGGCATCT CCGTCAAAAC TCTTGTCCCT GGTCTGTGGT AACTTTCTCA
16951  GCTCCCCAAC CCATGTCCCT CAAAGTCCCC TCCCTATAGG GCAAGAACCC
17001  AGCAACTTCG CTCTGCCCCG ACTCTAGGCG GGATGTAGCT CATTTTGGGA
17051  TACGAGTCTC CATCGTGGAG CCTGGCTTCT TCCGAACCCC TGTGACCAAC
17101  CTGGAGAGTC TGGAGAAAAC CCTGCAGGCC TGCTGGGCAC GGCTGCCTCC
17151  TGCCACACAG GCCCACTATG GGGGGGCCTT CCTCACCAAG TGTGAGTAGC
17201  CAGGCCCACA CAGGGGCACA TGAAGGGAAA CAAGTACCAG AAAGGCCAGT
17251  CCTGCATAAG CCTGCTAGGA GGTGGGTGGG GCACCCAGGG CAGGGTTGAG
17301  GGTGAACAGG ATGTTACAAN AGTGCCCAGG CCATGTGGAA CCTCCCCACT
17351  CCCCACACTG AGGAGGGGAC TGAGGGTGAC AAGCCCAGGG CCCCAGAAGA
17401  CAGTACCTAA GATGGGCTGG AGTGAGGAAG GGAAACTGAT TGCAACCACC
17451  TATGGGGCTG CAGACCTGAA AATGCAACAG CGCATCATGA ACCTGATCTG
17501  TGACCCGGAC CTAACCAAGG TGAGCCGATG CCTGGAGCAT GCCCTGACTG
17551  CTCGACACCC CCGAACCCGC TACAGCCCAG GTTGGGATGC CAAGCTGCTC
17601  TGGCTGCCTG CCTCCTACCT GCCAGCCAGC CTGGTGGATG CTGTGCTCAC
17651  CTGGGTCCTT CCCAAGCCTG CCCAAGCAGT CTACTGAATC CAGCCTTCCA
17701  GCAAGAGATT GTTTTTCAAG GACAAGGACT TTGATTTATT TCTGCCCCCA
17751  CCCTGGTACT GCCTGGTGCC TGCCACAAAA TAAGCACTAA CAAAAGTGTA
17801  TTGTTTAAAA AATAAAAAGA AGGTGGGCAG AAATGTGCCC AGTGGAAGGC
17851  TGACCCCATT TAAGTGCCAA CTACTCCAAA CCGACATGCT CACGGTCTCT
17901  GGCCTGTTCA GTCCCTGCAA AACAGCTAGC ACCCACAGTG GGGCGCCAGG
17951  GAACTGCCTC ACATCTACAG CTGCACGTCG GGGAGTGGCC ATCAAAGGGC
18001  ACTTTAATAC ATTTCCCTTA TTTTCTGAAG GGGAGTAAGG TTGCAATTCA
18051  GTGTCTGTAC TGGGAATGGT CTTCATATTT CTTGGGGGAG AAGAGCAGGT
18101  GATGAGGGTT CTGGGCCAGG CTGGGTGGCT TCCATGGAAG AAAAGGCAAT
18151  ATTCACATAA ATTCTCCTGC TAAGGACACT GACCACACAG GTGTCAAGGC
18201  AACTTATCAT ACTTCGAAAG GAGCTGGATC CCTTGAGGAT TGGCCAGGAA
18251  GGGAGGTGCT GGGCCCTTAG CGGTGCACAG AAGGCCAGGA AGATGTCCAA
18301  GGCAGATGGG GGCTGGGCTC TCGCAGGTGG GACCTTTCTG GGGAGCTGCT
18351  TTGACTTATG CAGCAGATGG CTTCATGAAT GTTCATAGTG AGCCTGGCAG
18401  CATAAGACTA GGGGGCAGAA AGCACCACAG TCTCTGGATC CTCACTTCTC
18451  CCACTGCCTG CCCAACCAAC ACCTTCGCAA AGTCCTCCTT TCCCAAACAC
18501  CCCCCAAAAT AGACCTCGAA GTACACATGC ATTAAGGTCC CAGAGGACAG
18551  GGAACATCAG TAAGGAAAGG AAGGAATCAA GCATCACTCT AAGACAAACT
18601  CAGACCATCT CTTTTCGGTC TGAAAAAATA ATCCGTTTAA TTGAAAAACC
18651  TGGAGGATAC TATTCCACTC CCCCAGATGA GGAGGCTGAG GAGACCAGAC
18701  CCCTACATCA CCTCGTAGCC ACTTCTGATA CTCTTCACGA GGCAGCAGGC
18751  AAAGACAATT CCCAAAACCT AGAAGGAAAG ATGGGGACAG GGGTGGAGAG
18801  GAGTCAGAAG GGCTAGCTAC CTCAGACCCA TGCAAGAGAC TCCAAACACA
18851  CACTCCCAGG CCAGTACCTC CTGTTCAGCA CCCTCCTCCC CTCAGCCCCC
```

FIGURE 3G

```
18901  TTCCCTCCAG GCAACCCTGG ACAGAGTCCC AGCCCCTGCT CAGGGTTATC
18951  TCTTACCTCG ACAAAAGCAA TTCCAAGGGC TGCTGCAGCT ACCACCAGCA
19001  CATTTTTCCT CAGCCAGCCC CCAATCTTCT CCACACAGCC CTGAAGGTGG
19051  CAGGCACAAA GGACAAAAGC ACCATCAGAA ACTTCCCACC CCAACCCCCT
19101  CCCTTGGTCC ATCAGTCTCT TCCCTGCCCC TGTACCTTTC ACCCCACCCT
19151  TAGCATTTCC AGATCCCCTC CCCATCCCTG ACCCTGTCCA CCTCCATCCT
19201  GGGTCTCTTG CATTCTAAAA CATTTCCCAG GTTTCCCAAG TCCCATACAC
19251  AGTCTCCTCC CTACCTCCTT ATGGATCGCC TTCTCGTTGA AATTAATCCC
19301  ACAGCCCACA GTAACATTAA TGCAGCAGGA GTCGGGGACT CGGTTCTTCG
19351  ACATGGAAGG GATTTTCTCC CAATCTGTGT AGTTAGCAGC CCCACAGCAC
19401  TTAAACTGGG GGAGGGAAGA AATATGGAGA AGAAGGTTGT TAAGTGAACC
19451  TTCACCTTCA ATATGGAGAT GAGAATTCTT TTTTTTTTTT TTTTTTTTTT
19501  TTTGAGACAG AGACTTGCTC TGTTGCCCAG ACAAGTGCCC AGCGGTGGCT
19551  CAATCTCGGC TCACTGCAAC CTCCGCCTCC CGGGTTCAAG CGATTCTCCT
19601  GCCTCACCCT CCTGAGTAGG TGGGATTACA GGCACTCACC ACCACACCTG
19651  GCTAATTTTT GTATTTTTAG TAGAGACAGG GTTTCACCAC GTTGGCCAGG
19701  CTAGTCTTGA ACTTCTGACC TCAGGTGATC TGCCCACCTC GGCCTTCAAA
19751  AGTGCTGAGA TTACAGGCGT GAGTCACCAC ACCCAGCCTT GGAGATGAGA
19801  ATTCTC (SEQ ID NO:3)
```

FEATURES:
Start:        1329
Exon: 1329    1389
Intron:       1390     3544
Exon: 3545    3546
Intron:       3551     17684
Exon: 3551    3618
Intron:       3619     5748
Exon: 5749    5881
Intron:       5882     8072
Exon: 8073    8241
Intron:       8242     8435
Exon: 8436    8694
Intron:       8695     17027
Exon: 17028   17191
Intron:       17192    17463
Exon: 17464   17684
Stop:  17685

SNPs:

| DNA Position | Major | Minor |   |
|---|---|---|---|
| 7440 | G | A |   |
| 7467 | A | G |   |
| 7469 | G | A |   |
| 8149 | A | G | C |
| 8741 | C | A |   |
| 16339 | A | C |   |
| 16928 | T | C |   |
| 17058 | C | G |   |
| 17170 | G | T |   |
| 17569 | A | G |   |
| 17610 | G | C |   |

FIGURE 3H

Context:

DNA
Position

7440  GGGCGCTGTAGTACCTGCCAGCTTTCGCCACAGGAGGTAAGTGGATACTGGGAGCTGGGG
GAACTGAGAAGACTAGCCAGATATTACATGTATTGCCAACTCAAAACTTTCAGCTTTTAA
CATGCTTCCTCACACATTATCCCCTTTGATCCTCCACAACTCTGAGGTGGACCTGGTGGG
TCTTAGCCCCACTTGGTAGATGAGAAAATAGGTTGAGAGAGACAGTGAGATGCTCAGTAT
CACACAGCAAACCTCTTGGCCCTATACATCATTCCAAACACAAGACCCAGGTTGCATATA
[G,A]
AAGGTTCAGTGTCCCTGGTTTAGAAGGAGAGGTGGTGTGAGGCAAGCAAGAAGATGCCTC
TGCTGCACTCCAGCCTGGGCGACAGAGTGAGACTCCATCTCAAAAAAAAAAAAAAAAAAA
AAAAGATGCCTCTGCTCCATACAGCAGGTCTGTACACAGGATCTGGCTCATGTGGTTTTA
GTTNNNNNNNNNNNNNNNNNNNNNNNNNNNNNNNNNNNNNNNNNNNNNNNNNNNNNNNN
NNNNNNNNNNNNNNNNNNNNNNTGGTTTTAGTTAAAGTTAGCCACAAATACAGCGTCTGCCC

7467  CCACAGGAGGTAAGTGGATACTGGGAGCTGGGGGAACTGAGAAGACTAGCCAGATATTAC
ATGTATTGCCAACTCAAAACTTTCAGCTTTTAACATGCTTCCTCACACATTATCCCCTTT
GATCCTCCACAACTCTGAGGTGGACCTGGTGGGTCTTAGCCCCACTTGGTAGATGAGAAA
ATAGGTTGAGAGAGACAGTGAGATGCTCAGTATCACACAGCAAACCTCTTGGCCCTATAC
ATCATTCCAAACACAAGACCCAGGTTGCATATAGAAGGTTCAGTGTCCCTGGTTTAGAAG
[A,G]
AGAGGTGGTGTGAGGCAAGCAAGAAGATGCCTCTGCTGCACTCCAGCCTGGGCGACAGAG
TGAGACTCCATCTCAAAAAAAAAAAAAAAAAAAAAAAGATGCCTCTGCTCCATACAGCAG
GTCTGTACACAGGATCTGGCTCATGTGGTTTTAGTTNNNNNNNNNNNNNNNNNNNNNNNN
NNNNNNNNNNNNNNNNNNNNNNNNNNNNNNNNNNNNNNNNNNNNNNNNNNNNNNNTGGTTTT
AGTTAAAGTTAGCCACAAATACAGCGTCTGCCCACATCTTTGCTTTGAACAGATGAGCCA

7469  ACAGGAGGTAAGTGGATACTGGGAGCTGGGGGAACTGAGAAGACTAGCCAGATATTACAT
GTATTGCCAACTCAAAACTTTCAGCTTTTAACATGCTTCCTCACACATTATCCCCTTTGA
TCCTCCACAACTCTGAGGTGGACCTGGTGGGTCTTAGCCCCACTTGGTAGATGAGAAAAT
AGGTTGAGAGAGACAGTGAGATGCTCAGTATCACACAGCAAACCTCTTGGCCCTATACAT
CATTCCAAACACAAGACCCAGGTTGCATATAGAAGGTTCAGTGTCCCTGGTTTAGAAGGA
[G,A]
AGGTGGTGTGAGGCAAGCAAGAAGATGCCTCTGCTGCACTCCAGCCTGGGCGACAGAGTG
AGACTCCATCTCAAAAAAAAAAAAAAAAAAAAAAAAGATGCCTCTGCTCCATACAGCAGGT
CTGTACACAGGATCTGGCTCATGTGGTTTTAGTTNNNNNNNNNNNNNNNNNNNNNNNNNN
NNNNNNNNNNNNNNNNNNNNNNNNNNNNNNNNNNNNNNNNNNNNNNNNNNNNTGGTTTTAG
TTAAAGTTAGCCACAAATACAGCGTCTGCCCACATCTTTGCTTTGAACAGATGAGCCATG

8149  AAAGGGCTTGAGGGCCACAGTAAACTGGACAAGTTTTTCTGCCCAGCCTAGGCTGCCACC
TGTAGGTCACTTGGGCTCCAGCTATGTGGCTGCCTCTTCTGCTGGGTGCCTTACTCTGGG
CAGTGCTGTGGTTGCTCAGGGACCGGCAGAGCCTGCCCGCCAGCAATGCCTTTGTCTTCA
TCACCGGCTGTGACTCAGGCTTTGGGCGCCTTCTGGCACTGCAGCTGGACCAGAGAGGCT
TCCGAGTCCTGGCCAGCTGCCTGACCCCCTCCGGGGCCGAGGACCTGCAGCGGGTGGCCT
[A,G,C]
CTCCCGCCTCCACACCACCCTGTTGGATATCACTGATCCCCAGAGCGTCCAGCAGGCAGC
CAAGTGGGTGGAGATGCACGTTAAGGAAGCAGGTAAGTATGGTAGACCACCAGGAATATG
GTGTGGGGTGTCCTGATCCCCACAGTCACCCCAGGAGTCACCTGCAAGGGCTGTGGTAAG
CTAAAGGGACAATTTGAGGAGAAGCAGTTTTTCAGATGCTCCCAGGAAGAAGAGGGAGCTG
TGGGAGTGCCCTCACCTACCCCCAGCATCCTTTTCATCTCCCCACAGGGCTTTTTGGTCTG

FIGURE 31

8741    TTTGGTCTGGTGAATAATGCTGGTGTGGCTGGTATCATCGGACCCACACCATGGCTGACC
CGGGACGATTTCCAGCGGGTGCTGAATGTGAACACAATGGGTCCCATTGGGGTCACCCTT
GCCCTGCTGCCTCTGCTGCAGCAAGCCCGGGGCCGGGTGATCAACATCACCAGCGTCCTG
GGTCGCCTGGCAGCCAATGGTGGGGGCTACTGTGTCTCCAAATTTGGCCTGGAGGCCTTC
TCTGACAGCCTGAGGTGAGGGGTACAGGGCTCTGGGTTCCAGGACTAACAGCAGCCCACT
[C,A]
AACAAACGTGGGCCAGCAGAGGTGGTTAAAATACAGCACATTGGAATAGTTAAAAAGAGA
CAGTTTAGGGCTAAACTTCATGGGTTCAATGAAGTCTACCCTTATGTAAGCTTTGTGAC

16339   AGCCTGCGTTTGTCACCATCACTCAGCAAATAACCTGAATGTCTCCTGTCTCTCAGCCTT
AATTTTTCAGGCAGCATCATGGGACACATACTTTTAGTTTTGAGACAAGGCCTTGCTCTC
ACCCAGGGTGGAGTGCAGTGGTGCAGTCACGGCCCACTGAACTTCAAACTCCTAGGCTCA
AGCAGCTCAAGCGATATCCGCCTCAGCCTCCTGAGTAGCTGAGACCACAGGCGCGTGCCA
GCATGCCTGGCTAGTATTTTTTTACAGATGGGGTCTTGCTGTGGTGACCAGACTTGTCTC
[A,C]
AACTCCCGGCCTCAAGCGATGCTTCCGCCTGGGCCTCCCAAAGTGTTGGGATTATAGGTG
TGAGCCACTGCATACTGGAACACATACTTTATACTTGAATTTTTTTTTATCCCCTTCCCT
CCTGCTCCTTACCTATACTTGGATTTCTACATCTGTGCCAGGGCAGTGGGATGTATCCCC
ACTTTCCCCATCAGCTTACCCTCCAGCAAATACGAGACTATACCCTTCAATATCCAGCAC
TCAGGGCTCAACCATGTGTTTTGGGAGCAAGGGAATGGGGTTCCTCTAGGTCAGGAATCG

16928   GGTCAGGAATCGGCAAACTCAGTACTCAAGCCAGATCTGGCCAGCTGCCTACAAGCTGAT
AATGGTTTTTTTTATTTTTAAATGGTTACATTGTAAACTGTTATATAAGTACCTGATAAT
ATCATTAATTTTGTTTCTTGGCCTGCCATGCTTAAAATATTAACTCTCTGGCCCTTTAAG
AAAAAAACGTGCTGACCCCTGCTCTAGATCAAAGAAAACAAACCTCAAAAATACTTTCCT
CCCTCTACCCCACTTGACCCTTGTCCCGGGGCAGTAGGCATCTCCGTCAAAACTCTTGTC
[T,C]
CTGGTCTGTGGTAACTTTCTCAGCTCCCCAACCCATGTCCCTCAAAGTCCCCTCCCTATA
GGGCAAGAACCCAGCAACTTCGCTCTGCCCCGACTCTAGGCGGGATGTAGCTCATTTTGG
GATACGAGTCTCCATCGTGGAGCCTGGCTTCTTCCGAACCCCTGTGACCAACCTGGAGAG
TCTGGAGAAACCCTGCAGGCCTGCTGGGCACGGCTGCCTCCTGCCACACAGGCCCACTA
TGGGGGGGCCTTCCTCACCAAGTGTGAGTAGCCAGGCCCACACAGGGGCACATGAAGGGA

17058   TTGTTTCTTGGCCTGCCATGCTTAAAATATTAACTCTCTGGCCCTTTAAGAAAAAAACGT
GCTGACCCCTGCTCTAGATCAAAGAAAACAAACCTCAAAAATACTTTCCTCCCTCTACCC
CACTTGACCCTTGTCCCGGGGCAGTAGGCATCTCCGTCAAAACTCTTGTCCCTGGTCTGT
GGTAACTTTCTCAGCTCCCCAACCCATGTCCCTCAAAGTCCCCTCCCTATAGGGCAAGAA
CCCAGCAACTTCGCTCTGCCCCGACTCTAGGCGGGATGTAGCTCATTTTGGGATACGAGT
[C,G]
TCCATCGTGGAGCCTGGCTTCTTCCGAACCCCTGTGACCAACCTGGAGAGTCTGGAGAAA
ACCCTGCAGGCCTGCTGGGCACGGCTGCCTCCTGCCACACAGGCCCACTATGGGGGGGCC
TTCCTCACCAAGTGTGAGTAGCCAGGCCCACACAGGGGCACATGAAGGGAAACAAGTACC
AGAAAGGCCAGTCCTGCATAAGCCTGCTAGGAGGTGGGTGGGGCACCCAGGGCAGGGTTG
AGGGTGAACAGGATGTTACAANAGTGCCCAGGCCATGTGGAACCTCCCCACTCCCCACAC

17170   CTCTACCCCACTTGACCCTTGTCCCGGGGCAGTAGGCATCTCCGTCAAAACTCTTGTCCC
TGGTCTGTGGTAACTTTCTCAGCTCCCCAACCCATGTCCCTCAAAGTCCCCTCCCTATAG
GGCAAGAACCCAGCAACTTCGCTCTGCCCCGACTCTAGGCGGGATGTAGCTCATTTTGGG
ATACGAGTCTCCATCGTGGAGCCTGGCTTCTTCCGAACCCCTGTGACCAACCTGGAGAGT
CTGGAGAAACCCTGCAGGCCTGCTGGGCACGGCTGCCTCCTGCCACACAGGCCCACTAT
[G,T]
GGGGGGCCTTCCTCACCAAGTGTGAGTAGCCAGGCCCACACAGGGGCACATGAAGGGAAA
CAAGTACCAGAAAGGCCAGTCCTGCATAAGCCTGCTAGGAGGTGGGTGGGGCACCCAGGG

FIGURE 3J

```
         CAGGGTTGAGGGTGAACAGGATGTTACAANAGTGCCCAGGCCATGTGGAACCTCCCCACT
         CCCCACACTGAGGAGGGGACTGAGGGTGACAAGCCCAGGGCCCCAGAAGACAGTACCTAA
         GATGGGCTGGAGTGAGGAAGGGAAACTGATTGCAACCACCTATGGGGCTGCAGACCTGAA

17569    GAGGTGGGTGGGGCACCCAGGGCAGGGTTGAGGGTGAACAGGATGTTACAANAGTGCCCA
         GGCCATGTGGAACCTCCCCACTCCCCACACTGAGGAGGGGACTGAGGGTGACAAGCCCAG
         GGCCCCAGAAGACAGTACCTAAGATGGGCTGGAGTGAGGAAGGGAAACTGATTGCAACCA
         CCTATGGGGCTGCAGACCTGAAAATGCAACAGCGCATCATGAACCTGATCTGTGACCCGG
         ACCTAACCAAGGTGAGCCGATGCCTGGAGCATGCCCTGACTGCTCGACACCCCCGAACCC
         [A,G]
         CTACAGCCCAGGTTGGGATGCCAAGCTGCTCTGGCTGCCTGCCTCCTACCTGCCAGCCAG
         CCTGGTGGATGCTGTGCTCACCTGGGTCCTTCCCAAGCCTGCCCAAGCAGTCTACTGAAT
         CCAGCCTTCCAGCAAGAGATTGTTTTTTCAAGGACAAGGACTTTGATTTATTTCTGCCCCC
         ACCCTGGTACTGCCTGGTGCCTGCCACAAAATAAGCACTAACAAAAGTGTATTGTTTAAA
         AAATAAAAAGAAGGTGGGCAGAAATGTGCCCAGTGGAAGGCTGACCCCATTTAAGTGCCA

17610    GATGTTACAANAGTGCCCAGGCCATGTGGAACCTCCCCACTCCCCACACTGAGGAGGGGA
         CTGAGGGTGACAAGCCCAGGGCCCCAGAAGACAGTACCTAAGATGGGCTGGAGTGAGGAA
         GGGAAACTGATTGCAACCACCTATGGGGCTGCAGACCTGAAAATGCAACAGCGCATCATG
         AACCTGATCTGTGACCCGGACCTAACCAAGGTGAGCCGATGCCTGGAGCATGCCCTGACT
         GCTCGACACCCCCGAACCCGCTACAGCCCAGGTTGGGATGCCAAGCTGCTCTGGCTGCCT
         [G,C]
         CCTCCTACCTGCCAGCCAGCCTGGTGGATGCTGTGCTCACCTGGGTCCTTCCCAAGCCTG
         CCCAAGCAGTCTACTGAATCCAGCCTTCCAGCAAGAGATTGTTTTTCAAGGACAAGGACT
         TTGATTTATTTCTGCCCCCACCCTGGTACTGCCTGGTGCCTGCCACAAAATAAGCACTAA
         CAAAAGTGTATTGTTTAAAAAATAAAAAGAAGGTGGGCAGAAATGTGCCCAGTGGAAGGC
         TGACCCCATTTAAGTGCCAACTACTCCAAACCGACATGCTCACGGTCTCTGGCCTGTTCA
```

FIGURE 3K

ISOLATED HUMAN DEHYDROGENASES, NUCLEIC ACID MOLECULES ENCODING THESE HUMAN DEHYDROGENASES, AND USES THEREOF

RELATED APPLICATIONS

The present application is a divisional of U.S. application Ser. No. 09/740,028, filed on Dec. 20, 2000, and issued on Jun. 25, 2002 as U.S. Pat. No. 6,410,289.

FIELD OF THE INVENTION

The present invention is in the field of dehydrogenases that are related to the retinol dehydrogenase subfamily, recombinant DNA molecules and protein production. The present invention specifically provides novel dehydrogenase polypeptides and proteins and nucleic acid molecules encoding such peptide and protein molecules, all of which are useful in the development of human therapeutics and diagnostic compositions and methods.

BACKGROUND OF THE INVENTION

Dehydrogenases, particularly members of the retinol dehydrogenase subfamilies, are a major target for drug action and development. Accordingly, it is valuable to the field of pharmaceutical development to identify and characterize previously unknown members of these subfamily of dehydrogenases. The present invention advances the state of the art by providing a previously unidentified human dehydrogenases that have homology to members of the retinol dehydrogenase subfamilies.

Dehydrogenases 17.beta.-hydroxysteroid dehydrogenase

The enzymes identified as 17.beta.-hydroxysteroid dehydrogenase (HSD) are important in the production of human sex steroids, including androst-5-ene-3.beta.,17.beta.-diol (.DELTA.sup.5-diol), testosterone and estradiol. In humans, several types of 17.beta.-HSD have now been identified and characterized. Each type of 17.beta.-HSD has been found to catalyze specific reactions and to be located in specific tissues. Further information about Types 1, 2 and 3 17.beta.-HSD can be had by reference as follows: Type 1 17.beta.-HSD is described by Luu-The, V. et al., Mol. Endocrinol., 3:1301–1309 (1989) and by Peltoketo, H. et al., FEBSLett, 239:73–77 (1988); Type 2 17.beta.-HSD is described in Wu, L. et al., J. Biol Chem, 268:12964–12969 (1993); Type 3 17.beta.-HSD is described in Geissler, W M, Nature Genetics, 7:34–39 (1994).

Inhibitors of 17.beta.-hydroxysteroid dehydrogenase activity can be used for prophylaxis or treatment of benign prostate hypertrophy (see WO publication 91/100731).

20-alpha-hydroxysteroid dehydroyenase

The enzyme responsible for the ovarian metabolism of progesterone to 20.alpha-hydroxyprogesterone is 20.alpha.-hydroxysteroid dehydrogenase (20.alpha.-HSD). Specifically, 20.alpha.-HSD is nicotinamide adenine dinucleotide phosphate (NADPH)-dependent and catalyzes the transfer of hydrogen from NADPH to progesterone.

By metabolizing progesterone to an inactive form, 20.alpha.-HSD plays a central role in inhibiting the maintenance of pregnancy and prevention of implantation [Wiest, Endocrinology 83:1181–184 (1968); Wiest et al., Endocrinology 82:844–859 (1968); Kuhn and Briley, i Biochem. J. 0117:193–200 (1970); Rodway and Kuhn, Biochem. J. 152:433–443 (1975)]. Further supporting this role is the fact that it is the increase in ovarian 20.alpha.-HSD activity rather than a decrease in the synthesis of progesterone that contributes to the lower circulating progesterone levels associated with the termination of pregnancy [Kuhn and Briley, Biochem. J. 117:193–201 (1970)]. Indeed, 20.alpha.-HSD gene expression [Albarracin et al. Endocrinology 134:2453–2460 (1994)] and activity remains repressed throughout pregnancy but are induced before parturition [Wiest et al., Endocrinology 82:844–859 (1968); Kuhn and Briley, Biochem. J. 117:193–200 (1970]. Also, ovarian 20.alpha.-HSD catalyzes the decline in progesterone levels which occur during normal and induced termination of pregnancy and pseudopregnancy [Hashimoto and Wiest, Endocrinology 84:873–885 (1969); Naito et al., Endocrinology Jpn 33(1):43–50 (February 1986)].

While 20.alpha.-HSD is of much interest as a key enzyme in the termination/prevention of pregnancy, it is possible that the enzyme is also of importance in spontaneous abortions. Specifically, it is possible that a significant number of spontaneous abortions are due to early expression of 20.alpha.-HSD. Therefore, detection of early 20.alpha.-HSD expression would be of interest in those susceptible to early spontaneous abortions. If detection is made early enough, progesterone replacement therapy could be initiated to help maintain the pregnancy.

11.beta.-hydroxysteroid dehydrogenase

Corticosteroids, also referred to as glucocorticoids, are steroid hormones, the most common form of which is cortisol. Modulation of glucocorticoid activity is important in regulating physiological processes in a wide range of tissues and organs. Glucocorticoids act within the gonads to directly suppress testosterone production (Monder et al., 1994). High levels of glucocorticoids may also result in excessive salt and water retention by the kidneys, producing high blood pressure.

Glucocorticoid action is mediated via binding of the molecule to a receptor, such as either a mineralocorticoid receptor (MR) or a glucocorticoid receptor (GR). Krozowski et al. (1983) and Beaumont and Fanestil (1983) showed that MR of adrenalectomised rats have an equal affinity for the mineralocorticoid aldosterone and glucocorticoids, for example corticosterone and cortisol. Confirmatory evidence has been found for human MR (Arriza et al., 1988). In patients suffering from the congenital syndrome of Apparent Mineralocorticoid Excess (AME; Ulick et al., 1979), cortisol levels are elevated and bind to and activate MRs normally occupied by aldosterone, the steroid that regulates salt and water balance in the body. Salt and water are retained in AME patients causing severe hypertension.

The enzyme 11.beta.-hydroxysteroid dehydrogenase (11.beta.HSD) converts glucocorticoids into metabolites that are unable to bind to MRs Edwards et al., 1988; Funder et al., 1988), present in mineralocorticoid target tissues, for example kidney, pancreas, small intestine, colon, as well as the hippocampus, placenta and gonads. For example, in aldosterone target tissues 11.beta.HSD inactivates glucocorticoid molecules, allowing the much lower circulating levels of aldosterone to maintain renal homeostasis. When the 11.beta.HSD enzyme is inactivated, for example in AME patients Ulick et al., 1979) or following administration of glycyrrhetinic acid, a component of licorice, severe hypertension results. Further, placental 11.beta.HSD activity may protect the foetus from high circulating levels of glucocorticoid which may predispose to hypertension in later life Edwards et al., 1993).

Biochemical characterisation of 11.beta.HSD activity indicates the presence of at least two isoenzymes (11.beta.HSD1 and 11.beta.HSD2) with different cofactor requirements and substrate affinities. The 11.beta.HSD1 enzyme is a low affinity enzyme that prefers NADP+ as a cofactor (Agarwal et al., 1989). The 11.beta.HSD2 enzyme is a high affinity enzyme (Km for glucocorticoid=10 nM), requiring NAD+, not NADP+ as the preferred cofactor, belonging to a class of glucocorticoid dehydrogenase enzymes hereinafter referred to as "NAD+ dependent glucocorticoid dehydrogenase" enzymes.

Michael et al. (1993) show an inverse correlation between 11.beta.HSD enzyme activity in human granulosa-lutein cells and the success of IVF (in vitro fertilization), and suggest that activity of this enzyme might be related to the success of embryo attachment and implantation following IVF. The measurement of ovarian 11.beta.HSD enzyme activity as a prognostic indicator for the outcome of assisted conception in all species, is the subject of UK Patent Application No 9305984.

3alpha-hydroxysteroid dehydrogenase

Human liver 3alpha-hydroxysteroid plays an important role in the metabolism of steroid hormones and polycyclic aromatic hydrocarbons and in the reduction of ketone-containing drugs (Kume et al., Pharmacogenetics 1999 December; 9(6):763–71). 3alpha-hydroxysteroid is also involved in the metabolism of bile acids (Yamamoto et al., Biol Pharm Bull 1998 November; 21(11):1148–53).

3alpha-hydroxysteroid plays a significant role in 5alpha-dihydrotestosterone metabolism in human liver via 3alpha-hydroxysteroid reduction, followed by subsequent glucuronidation and clearance via the kidney (Pirog et al., J Clin Endocrinol Metab 1999 September; 84(9):3217–21).

Trans-1,2-dihydrobenzene-1,2-diol dehydrogenase

Two major forms of trans-1,2-dihydrobenzene-1,2-diol dehydrogenase exist. One form shows strict specificity for benzene dihydrodiol and NADP+. The other form oxidizes n-butanol, glycerol, sorbitol, and benzene dihydrodiol in the presence of NADP+ or NAD+, and exhibits high reductase activity towards aldehydes, aldoses and diacetyls (Matsuura et al., Biochim Biophys Acta 1987 April 8; 912(2):270–7).

3-oxo-5-beta-steroid 4 dehydrogenase (also referred to as delta 4-3-Ketosteroid 5 beta-reductase)

3-oxo-5-beta-steroid 4 dehydrogenase exhibits activity toward a variety of substrates, including testosterone, cortisol, cortisone, progesterone, 4-androstene-3,17-dione, 7 alpha-hydroxy-4-cholesten-3-one, and 7 alpha, 12 alpha-dihydroxy-4-cholesten-3-one (Okuda et al., J Biol Chem 1984 June. 25;259(12):7519–24).

Retinol dehydrogenase

Vitamin A is a pigment essential to vision. Vitamin A comes from the enzymatic conversion of carotenoids, yellow pigments common to carrots and other vegetables, to retinol. Deficiency of vitamin A and insufficient retinol production leads to a variety of maladies in humans and experimental animals. Symptoms of deficiency include vision related disorders such as xerophthalmia and night blindness; dry skin and dry mucous membranes; retarded development and growth; and sterility in male animals.

Cleavage of .beta.-carotene yields two molecules of retinol; oxidation of retinol forms retinal. Retinal and opsin combine to produce rhodopsin, a visual pigment found in nature. The excitation of rhodopsin with visible light triggers a series of photochemical reactions and conformational changes in the molecule which result in the electrical signal to the brain that are the basis of visual transduction (Lehninger et al. (1993) Principles of Biochemistry, Worth Publishers, New York, N.Y.).

Retinol dehydrogenase (RoDH) catalyzes the conversion of retinol to retinal; retinal dehydrogenase converts retinal to retinoate. Retinoate is a retinoid and a hormone which controls numerous biological processes by regulating eukaryotic gene expression. Retinoids, like steroid and thyroid hormones, diffuse directly across the plasma membrane and bind to intracellular receptor proteins. Binding activates the receptors which interact with signaling pathways (Vettermann et al. (1997) Mol. Carcinog. 20: 58–67), and regulate the transcription of specific genes, particularly those mediating vertebrate development (Alberts et al. (1994) Molecular Biology of the Cell, Garland Publishing, Inc., New York, N.Y.). Retinol is known to be important in epithelial development (Haselbeck et al. (1997) Dev. Dyn. 208: 447–453; and Attar et al. (1997) Mol. Endocrinol. 11: 792–800) and in the development of the central nervous system (Maden et al. (1997) Development 124: 2799–2805). In Maden's studies on quail embryos, absence of vitamin A, lead to severe deficits including lack of a posterior hindbrain. Conversely, injection of retinol before gastrulation of the embryo prevented positional apoptosis and corrected the CNS defects.

The universal chromophore of visual pigments is 11-cis retinaldehyde which is generated by 11-cis retinol dehydrogenase, a membrane-bound enzyme abundantly expressed in the retinal pigment epithelium of the eye. The gene which encodes 11-cis retinol dehydrogenase may be involved in hereditary eye diseases (Simon et al. (1996) Genomics 36: 424–430).

Chai et al. have identified, cloned, and expressed two isoforms of retinol dehydrogenase, RoDH(I) and (RoDH(II) (1995, J. Biol. Chem. 270: 28408–28412). The deduced amino acid sequence shows that RoDH(I) and RoDH(II) are short-chain dehydrogenases/reductases that share 82% identity. Retinol is the substrate for RoDH(II) which has a higher affinity for NADP than NAD and is stimulated by ethanol and phosphatidyl choline. Although RoDH(II) is not inhibited by the medium-chain alcohol dehydrogenase inhibitor, 4-methylpyrazole, it is inhibited by phenylarsine oxide and carbenoxolone. Chai et al. reported detection of RoDH(I) and RoDH(II) mRNA in rat liver, but RNase protection assays revealed RoDH(I) and RoHD(II) mRNA in kidney, lung, testis, and brain. Based on these data, Chai et al. concluded that RoDH has tissue specific expression.

The retinol signaling pathway plays an important role in human disorders and diseases. Retinoic acid receptors (RARs; -alpha, -beta, and -gamma) are retinoid-activated transcription factors, which mediate effects of retinoids on gene expression. Alterations in receptor expression or function could interfere with the retinoid signaling pathway. Interference with the pathway may enhance cancer development. Vitamin A analogs (retinoids) which interact with RARs, suppress oral and lung carcinogenesis in animal models and prevent the development of tumors in head, neck, and lung cancer patients (Lotan R. 1997 Environ. Heath Perspect. 105 Suppl. 4: 985–988). Lotan reported that RAR beta expression is lost at early stages of carcinogenesis in the aerodigestive tract.

Retinol dehydrogenase may be implicated in embryonic development. The studies of Maden et al. (supra) suggest that retinol may play a significant role in controlling apoptosis during development of the central nervous system. Retinoids are also implicated in epidermal by development. Attar et al. (1997, Mol. Endocrinol. 11: 792–800) showed that disruption of epidermal barrier function results in extremely high incidences of neonatal mortality in pups.

In addition, retinol dehydrogenase activity is linked to hereditary eye diseases (Simon et al. (1996) Genomics 36: 424–430). Autosomal recessive childhood-onset severe retinal dystrophy (arCSRD) is a heterogeneous group of disorders that affect rod and cone photoreceptors simultaneously. Disease genes implicated in arCSRD are expected to encode proteins present in the neuroretina or in the retinal pigment epithelium (RPE). RPE65, a tissue-specific and evolutionarily highly conserved 61 kD protein, is the first disease gene in this group of inherited disorders that is expressed exclusively in RPE, and may play a role in vitamin A metabolism of the retina (Gu et al. (1997) Nat. Genet. 17: 194–197).

Pityriasis rubra pilaris (PRP) is an idiopathic erythematous scaling eruption which can be difficult to distinguish from psoriasis. The expression of RoDH(II) in the retinol signaling pathway may be of pathogenetic importance in the diagnosis of PRP (Magro, C. M. and Crowson, A. N. (1997) J. Cutan. Pathol. 24: 416–424).

The discovery of a new human retinol dehydrogenase and the polynucleotides encoding it satisfies a need in the art by providing new compositions which are useful in the diagnosis, prevention and treatment of disorders associated with immune response, cell proliferation, and development.

Substantial chemical and structural homology exists between the protein described herein and 11-cis retinol dehydrogenase (see FIG. 1). 11-cis retinol dehydrogenase are known in the art to be involved in retinal degeneration. For more information relating to the protein of the present invention, see Simon et al., Genomics 1996 September 15;36(3):424–30A, Yamamoto et al., Nat Genet 1999 June; 22(2):188–91H.

Dehydrogenase proteins, particularly members of the retinol dehydrogenase subfamily, are a major target for drug action and development. Accordingly, it is valuable to the field of pharmaceutical development to identify and characterize previously unknown members of this subfamily of dehydrogenase proteins. The present invention advances the state of the art by providing a previously unidentified human dehydrogenase proteins that have homology to members of the retinol dehydrogenase subfamily.

SUMMARY OF THE INVENTION

The present invention is based in part on the identification of amino acid sequences of human dehydrogenase polypeptides and proteins that are related to the 11-cis retinol dehydrogenase, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate dehydrogenase activity in cells and tissues that express the dehydrogenase. Experimental data as provided in FIG. 1 indicates expression in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma and human leukocyte.

DESCRIPTION OF THE FIGURE SHEETS

FIG. 1 provides the nucleotide sequence of a cDNA molecule sequence that encodes the dehydrogenase of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma and human leukocyte.

FIG. 2 provides the predicted amino acid sequence of the dehydrogenase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the dehydrogenase of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 11 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a dehydrogenase or part of a dehydrogenase and are related to the retinol dehydrogenase subfamily. Utilizing these sequences, additional genomic sequences were assembled and transcript and/or cDNA sequences were isolated and characterized. Based on this analysis, the present invention provides amino acid sequences of human dehydrogenase polypeptides that are related to the retinol dehydrogenase subfamily, nucleic acid sequences in the form of transcript sequences, cDNA sequences and/or genomic sequences that encode these dehydrogenase polypeptide, nucleic acid variation (allelic information), tissue distribution of expression, and information about the closest art known protein/peptide/domain that has structural or sequence homology to the dehydrogenase of the present invention.

In addition to being previously unknown, the peptides that are provided in the present invention are selected based on their ability to be used for the development of commercially important products and services. Specifically, the present peptides are selected based on homology and/or structural relatedness to known dehydrogenases of the retinol dehydrogenase subfamily and the expression pattern observed. Experimental data as provided in FIG. 1 indicates expression in the malignant melanoma (metastatic to lymph node), brain (glioblastoma), thyroid, colon tumor (RER+), stomach (poorly differentiated adenocarcinoma ran with signet ring cell features), primary B-cells from tonsils, lung carcinoid, Burkitt lymphoma and human leukocyte. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known retinol dehydrogenase family or subfamily of dehydrogenases.

SPECIFIC EMBODIMENTS

Peptide Molecules

The present invention provides nucleic acid sequences that encode protein molecules that have been identified as being members of the dehydrogenase family and are related to the retinol dehydrogenase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the dehydrogenases or peptides of the present invention, dehydrogenases or peptides, or peptides/proteins of the present invention.

The present invention provides isolated peptide and protein molecules that consist of, consist essentially of, or comprise the amino acid sequences of the dehydrogenase polypeptide disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components.

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the dehydrogenase polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated dehydrogenase polypeptide can be purified from cells that naturally express it, purified from cells that have been altered to express it (recombinant), or synthesized using known protein synthesis methods. Experimental data as provided in FIG. 1 indicates expression in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma and human leukocyte. For example, a nucleic acid molecule encoding the dehydrogenase polypeptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the dehydrogenase polypeptide of the present invention are the naturally occurring mature proteins. A brief description of how various types of these proteins can be made/isolated is provided below.

The dehydrogenase polypeptides of the present invention can be attached to heterologous sequences to form chimeric or fusion proteins. Such chimeric and fusion proteins comprise a dehydrogenase polypeptide operatively linked to a heterologous protein having an amino acid sequence not substantially homologous to the dehydrogenase polypeptide. "Operatively linked" indicates that the dehydrogenase polypeptide and the heterologous protein are fused in-frame. The heterologous protein can be fused to the N-terminus or C-terminus of the dehydrogenase polypeptide.

In some uses, the fusion protein does not affect the activity of the dehydrogenase polypeptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant dehydrogenase polypeptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A dehydrogenase polypeptide-encoding nucleic acid can be cloned into such an expression vector such that the fusion moiety is linked in-frame to the dehydrogenase polypeptide.

As mentioned above, the present invention also provides and enables obvious variants of the amino acid sequence of the peptides of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art know techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the dehydrogenase polypeptides of the present invention. The degree of homology/identity present will be based primarily on whether the peptide is a functional variant or non-functional variant, the amount of divergence present in the paralog family, and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two amino acid sequences is determined using the Needleman and Wunsch (J. Mol. Biol. (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., Nucleic Acids Res. 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can farther be used as a "query sequence" to perform a search against sequence databases to, for example, identify other family members or related sequences. Such searches can be performed using the NBLAST and XBLAST programs (version 2.0) of Altschul, et al. (J. Mol. Biol. 215:403–10 (1990)). BLAST nucleotide searches can be performed with the NBLAST program, score=100, word length=12 to obtain nucleotide sequences homologous to the nucleic acid molecules of the invention. BLAST protein searches can be performed with the XBLAST program, score=50, word length=3, to obtain amino acid sequences homologous to the proteins of the invention. To obtain gapped alignments for comparison purposes, Gapped BLAST can be utilized as described in Altschul et al. (Nucleic Acids Res. 25(17):3389–3402 (1997)). When utilizing BLAST and gapped BLAST programs, the default parameters of the respective programs (e.g., XBLAST and NBLAST) can be used. See http://www.ncbi.nlm.nih.gov.

Full-length pre-processed forms, as well as mature processed forms, of proteins that comprise one of the peptides of the present invention can readily be identified as having complete sequence identity to one of the dehydrogenase polypeptides of the present invention as well as being encoded by the same genetic locus as the dehydrogenase polypeptide provided herein.

Allelic variants of a dehydrogenase polypeptide can readily be identified as being a human protein having a high degree (significant) of sequence homology/identity to at least a portion of the dehydrogenase polypeptide as well as being encoded by the same genetic locus as the dehydrogenase polypeptide provided herein. Genetic locus can readily be determined based on the genomic information provided in FIG. 3, such as the genomic sequence mapped to the reference human. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a dehydrogenase polypeptide encoding nucleic acid molecule under stringent conditions as more fully described below.

FIG. 3 provides information on SNPs that have been found in the gene encoding the transporter protein of the present invention. SNPs were identified at 11 different nucleotide positions in introns and regions 5' and 3' of the ORF. Such SNPs in introns and outside the ORF may affect control/regulatory elements. The changes in the amino acid sequence that these SNPs cause can readily be determined using the universal genetic code and the protein sequence provided in FIG. 2 as a base.

Paralogs of a dehydrogenase polypeptide can readily be identified as having some degree of significant sequence homology/identity to at least a portion of the dehydrogenase polypeptide, as being encoded by a gene from humans, and as having similar activity or function. Two proteins will typically be considered paralogs when the amino acid sequences are typically at least about 40–50%, 50–60%, and more typically at least about 60–70% or more homologous through a given region or domain. Such paralogs will be encoded by a nucleic acid sequence that will hybridize to a dehydrogenase polypeptide encoding nucleic acid molecule under moderate to stringent conditions as more fully described below.

Orthologs of a dehydrogenase polypeptide can readily be identified as having some degree of significant sequence homology/identity to at least a portion of the dehydrogenase polypeptide as well as being encoded by a gene from another organism. Preferred orthologs will be isolated from mammals, preferably primates, for the development of human therapeutic targets and agents. Such orthologs will be encoded by a nucleic acid sequence that will hybridize to a dehydrogenase polypeptide encoding nucleic acid molecule under moderate to stringent conditions, as more fully described below, depending on the degree of relatedness of the two organisms yielding the proteins.

Non-naturally occurring variants of the dehydrogenase polypeptides of the present invention can readily be generated using recombinant techniques. Such variants include, but are not limited to deletions, additions and substitutions in the amino acid sequence of the dehydrogenase polypeptide. For example, one class of substitutions is conserved amino acid substitutions. Such substitutions are those that substitute a given amino acid in a dehydrogenase polypeptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent are found in Bowie et al., *Science* 247:1306–1310 (1990).

Variant dehydrogenase polypeptides can be fully functional or can lack function in one or more activities. Fully functional variants typically contain only conservative variations or variations in noncritical residues or in noncritical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallography, nuclear magnetic resonance, or photoaffinity labeling (Smith et al., *J. Mol. Biol.* 224:899–904 (1992); de Vos et al. *Science* 255:306–312 (1992)).

The present invention further provides fragments of the dehydrogenase polypeptides, in addition to proteins and peptides that comprise and consist of such figments. Particularly those comprising the residues identified in FIG. 2. The fragments to which the invention pertains, however, are not to be construed as encompassing fragments that have been disclosed publicly prior to the present invention.

As used herein, a fragment comprises at least 8, 10, 12, 14, 16 or more contiguous amino acid residues from a dehydrogenase polypeptide. Such fragments can be chosen based on the ability to retain one or more of the biological activities of the dehydrogenase polypeptide, or can be chosen for the ability to perform a function, e.g., act as an immunogen. Particularly important fragments are biologically active fragments, peptides that are, for example about 8 or more amino acids in length. Such fragments will typically comprise a domain or motif of the dehydrogenase polypeptide, e.g., active site. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE, HMMer, eMOTIF, etc.). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in dehydrogenase polypeptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties, 2nd Ed., T. E. Creighton, W. H. Freeman and Company, New York (1993). Many detailed reviews are available on this subject, such as by Wold, F., Posttranslational Covalent Modification of Proteins, B. C. Johnson, Ed., Academic Press, New York 1–12 (1983); Seifter et al. (Meth. Enzymol. 182: 626–646 (1990)) and Rattan et al. (Ann. N.Y. Acad. Sci. 663:48–62 (1992)).

Accordingly, the dehydrogenase polypeptides of the present invention also encompass derivatives or analogs in which a substituted amnino acid residue is not one encoded by the genetic code, in which a substituent group is included, in which the mature dehydrogenase polypeptide is fused with another compound, such as a compound to increase the half-life of the dehydrogenase polypeptide (for example, polyethylene glycol), or in which the additional amino acids are fused to the mature dehydrogenase polypeptide, such as a leader or secretory sequence or a sequence for purification of the mature dehydrogenase polypeptide, or a pro-protein sequence.

Protein/Peptide Uses

The proteins of the present invention can be used in assays to determine the biological activity of the protein, including in a panel of multiple proteins for high-throughput screening; to raise antibodies or to elicit another immune response; as a reagent (including the labeled reagent) in assays designed to quantitatively determine levels of the protein (or its ligand or receptor) in biological fluids; and as markers for tissues in which the corresponding protein is preferentially expressed (either constitutively or at a particular stage of tissue differentiation or development or in a disease state). Where the protein binds or potentially binds to another protein (such as, for example, in a receptor-ligand interaction), the protein can be used to identify the binding partner so as to develop a system to identify inhibitors of the binding interaction. Any or all of these research utilities are capable of being developed into reagent grade or kit format for commercialization as research products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, dehydrogenases isolated from humans and their human/mammalian orthologs serve as targets for identifying agents for use in mammalian therapeutic applications, e.g. a human drug, particularly in modulating a biological or pathological response in a cell or tissue that expresses the dehydrogenase. Experimental data as provided in FIG. 1 indicates that dehydrogenases of the present invention are expressed in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma detected by a virtual northern blot. In addition, PCR-based tissue screening panel indicates expression in human leukocyte. A large percentage of pharmaceutical agents are being developed that modulate the activity of dehydrogenases, particularly members of the retinol dehydrogenase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma and human in leukocyte. Such uses can readily be determined using the information provided herein, that which is known in the art, and routine experimentation.

The proteins of the present invention (including variants and fragments that may have been disclosed prior to the present invention) are useful for biological assays related to dehydrogenases that are related to members of the retinol dehydrogenase subfamily. Such assays involve any of the known dehydrogenase functions or activities or properties useful for diagnosis and treatment of dehydrogenase-related conditions that are specific for the subfamily of dehydrogenases that the one of the present invention belongs to, particularly in cells and tissues that express the dehydrogenase. Experimental data as provided in FIG. 1 indicates that dehydrogenases of the present invention are expressed in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma detected by a virtual northern blot. In addition, PCR-based tissue screening panel indicates expression in human leukocyte.

The proteins of the present invention are also useful in drug screening assays, in cell-based or cell-free systems. Cell-based systems can be native, i.e., cells that normally express the dehydrogenase, as a biopsy or expanded in cell culture. Experimental data as provided in FIG. 1 indicates expression in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma and human leukocyte. In an alternate embodiment, cell-based assays involve recombinant host cells expressing the dehydrogenase.

The polypeptides can be used to identify compounds that modulate dehydrogenase activity. Both the dehydrogenase of the present invention and appropriate variants and fragments can be used in high-throughput screens to assay candidate compounds for the ability to bind to the dehydrogenase. These compounds can be further screened against a functional dehydrogenase to determine the effect of the compound on the dehydrogenase activity. Further, these compounds can be tested in animal or invertebrate systems to determine activity/effectiveness. Compounds can be identified that activate (agonist) or inactivate (antagonist) the dehydrogenase to a desired degree.

Therefore, in one embodiment, retinol dehydrogenase or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising retinol dehydrogenase may be administered to a subject to prevent or treat a disorder associated with increased apoptosis including, but not limited to, those listed above.

In still another embodiment, an agonist which is specific for retinol dehydrogenase may be administered to prevent or treat a disorder associated with increased apoptosis including, but not limited to, those listed above.

In a further embodiment, a vector capable of expressing retinol dehydrogenase, or a fragment or a derivative thereof, may be used to prevent or treat a disorder associated with increased apoptosis including, but not limited to, those listed above.

In cancer, where retinol dehydrogenase promotes cell proliferation, it is desirable to decrease its activity. Therefore, in one embodiment, an antagonist of retinol dehydrogenase may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for retinol dehydrogenase may be used directly as an antagonist, or indirectly as a targeting or delivery mechanism for bringing a pharmaceutical agent to cells or tissue which express retinol dehydrogenase.

In another embodiment, a vector expressing the complement of the polynucleotide encoding retinol dehydrogenase may be administered to a subject to prevent or treat a cancer including, but not limited to, the types of cancer listed above.

In inflammation, where retinol dehydrogenase promotes cell proliferation, it is desirable to decrease its activity. Therefore, in one embodiment, an antagonist of retinol dehydrogenase may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for retinol dehydrogenase may be used directly as an antagonist, or indirectly as a targeting or delivery mechanism for bringing a pharmaceutical agent to cells or tissue which express retinol dehydrogenase.

Further, the dehydrogenase polypeptides can be used to screen a compound for the ability to stimulate or inhibit interaction between the dehydrogenase and a molecule that normally interacts with the dehydrogenase, e.g. a ligand or a component of the signal pathway that the dehydrogenase normally interacts. Such assays typically include the steps of combining the dehydrogenase with a candidate compound under conditions that allow the dehydrogenase, or fragment, to interact with the target molecule, and to detect the formation of a complex between the protein and the target or to detect the biochemical consequence of the interaction with the dehydrogenase and the target, such as any of the associated effects of signal transduction.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries). (Hodgson, Bio/technology, 1992, September 10 (9);973–80).

One candidate compound is a soluble fragment of the dehydrogenase that competes for ligand binding. Other candidate compounds include mutant dehydrogenases or appropriate fragments containing mutations that affect dehydrogenase function and thus compete for ligand. Accordingly, a fragment that competes for ligand, for example with a higher affinity, or a fragment that binds ligand but does not allow release, is within the scope of the invention.

The invention further includes other end point assays to identify compounds that modulate (stimulate or inhibit) dehydrogenase activity. The assays typically involve an assay of events in the dehydrogenase mediated signal transduction pathway that indicate dehydrogenase activity. Thus, the phosphorylation of a protein/ligand target, the expression of genes that are up- or down-regulated in response to the dehydrogenase dependent signal cascade can be assayed. In one embodiment, the regulatory region of such genes can be operably linked to a marker that is easily detectable, such as luciferase. Alternatively, phosphorylation of the dehydrogenase, or a dehydrogenase target, could also be measured.

Any of the biological or biochemical functions mediated by the dehydrogenase can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric dehydrogenases in which any of the protein's domains, or parts thereof, can be replaced by heterologous domains or subregions. Accordingly, a different set of signal transduction components is available as an end-point assay for activation. This allows for assays to be performed in other than the specific host cell from which the dehydrogenase is derived.

The dehydrogenase polypeptide of the present invention is also useful in competition binding assays in methods designed to discover compounds that interact with the dehydrogenase. Thus, a compound is exposed to a dehydrogenase polypeptide under conditions that allow the compound to bind or to otherwise interact with the polypeptide. Soluble dehydrogenase polypeptide is also added to the mixture. If the test compound interacts with the soluble dehydrogenase polypeptide, it decreases the amount of complex formed or activity from the dehydrogenase target. This type of assay is particularly useful in cases in which compounds are sought that interact with specific regions of the dehydrogenase. Thus, the soluble polypeptide that competes with the target dehydrogenase region is designed to contain peptide sequences corresponding to the region of interest.

To perform cell free drug screening assays, it is sometimes desirable to immobilize either the dehydrogenase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/15625 fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of dehydrogenase-binding protein found in the bead fraction quantitated from the gel using standard electrophoretic techniques. For example, either the polypeptide or its target molecule can be immobilized utilizing conjugation of biotin and streptavidin with techniques well known in the art. Alternatively, antibodies reactive with the protein but which do not interfere with binding of the protein to its target molecule can be derivatized to the wells of the plate, and the protein trapped in the wells by antibody conjugation. Preparations of a dehydrogenase-binding protein and a candidate compound are incubated in the dehydrogenase-presenting wells and the amount of complex trapped in the well can be quantitated. Methods for detecting such complexes, in addition to those described above for the GST-immobilized complexes, include immunodetection of complexes using antibodies reactive with the dehydrogenase target molecule, or which are reactive with dehydrogenase and compete with the target molecule, as well as enzyme-linked assays which rely on detecting an enzymatic activity associated with the target molecule.

Agents that modulate one of the dehydrogenases of the present invention can be identified using one or more of the above assays, alone or in combination. It is generally preferable to use a cell-based or cell free system first and then confirm activity in an animal/insect model system. Such model systems are well known in the art and can readily be employed in this context.

Modulators of dehydrogenase activity identified according to these drug screening assays can be used to treat a subject with a disorder mediated by the dehydrogenase associated pathway, by treating cells that express the dehydrogenase. Experimental data as provided in FIG. 1 indicates expression in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma and human leukocyte. These methods of treatment include the steps of administering the modulators of protein activity in a pharmaceutical composition as described herein, to a subject in need of such treatment.

In yet another aspect of the invention, the dehydrogenases can be used as "bait proteins" in a two-hybrid assay or three-hybrid assay (see, e.g., U.S. Pat. No. 5,283,317; Zervos et al., Cell 72:223–232 (1993); Madura et al., J. Biol. Chem. 268:12046–12054 (1993); Bartel et al., Biotechniques 14:920–924 (1993); Iwabuchi et al., Oncogene 8:1693–1696 (1993); and Brent WO94/10300), to identify other proteins that bind to or interact with the dehydrogenase and are involved in dehydrogenase activity. Such dehydrogenase-binding proteins are also likely to be involved in the propagation of signals by the dehydrogenases or dehydrogenase targets as, for example, downstream elements of a dehydrogenase-mediated signaling pathway, e.g., a pain signaling pathway. Alternatively, such dehydrogenase-binding proteins are likely to be dehydrogenase inhibitors.

The two-hybrid system is based on the modular nature of most transcription factors, which consist of separable DNA-binding and activation domains. Briefly, the assay utilizes two different DNA constructs. In one construct, the gene that codes for a dehydrogenase is fused to a gene encoding the DNA binding domain of a known transcription factor (e.g., GAL4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a dehydrogenase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the dehydrogenase.

This invention further pertains to novel agents identified by the above-described screening assays. Accordingly, it is within the scope of this invention to further use an agent identified as described herein in an appropriate animal model. For example, an agent identified as described herein (e.g., a dehydrogenase modulating agent, an antisense dehydrogenase nucleic acid molecule, a dehydrogenase-specific antibody, or a dehydrogenase-binding partner) can be used in an animal or insect model to determine the efficacy, toxicity, or side effects of treatment with such an agent. Alternatively, an agent identified as described herein can be used in an animal or insect model to determine the mechanism of action of such an agent. Furthermore, this invention pertains to uses of novel agents identified by the above-described screening assays for treatments as described herein.

The dehydrogenases of the present invention are also useful to provide a target for diagnosing a disease or predisposition to a disease mediated by the peptide, Accordingly, the invention provides methods for detecting the presence, or levels of, the protein (or encoding mRNA) in a cell, tissue, or organism. Experimental data as provided in FIG. 1 indicates expression in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma and human leukocyte. The method involves contacting a biological sample with a compound capable of interacting with the receptor protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells, and fluids present within a subject.

The peptides also are useful to provide a target for diagnosing a disease or predisposition to a disease mediated by the peptide, Accordingly, the invention provides methods for detecting the presence, or levels of, the protein in a cell, tissue, or organism. The method involves contacting a biological sample with a compound capable of interacting with the receptor protein such that the interaction can be detected.

The peptides of the present invention also provide targets for diagnosing active disease, or predisposition to a disease, in a patient having a variant peptide. Thus, the peptide can be isolated from a biological sample and assayed for the presence of a genetic mutation that results in translation of an aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered receptor activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations, and immunofluorescence using a detection reagents, such as an antibody or protein binding agent. Alternatively, the peptide can be detected in vivo in a subject by introducing into the subject a labeled anti-peptide antibody. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and receptor activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma and human leukocyte. Accordingly, methods for treatment include the use of the dehydrogenase or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')2, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the dehydrogenases. Antibodies can be prepared from any region of the peptide as described herein. However, preferred regions will include those involved in function/activity and/or receptor/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2)

Detection of an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S, or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that dehydrogenases of the present invention are expressed in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma detected by a virtual northern blot. In addition, PCR-based tissue screening panel indicates expression in human leukocyte. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development Antibody detection of circulating fragments of the full-length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma and human leukocyte. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the malignant melanoma (metastic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma and human leukocyte. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma and human leukocyte. Thus, where a specific protein has been correlated with expression in a specific tissue, antibodies that are specific for this protein can be used to identify a tissue type.

The antibodies are also useful for inhibiting protein function, for example, blocking the binding of the dehydrogenase to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use.

Nucleic Acid Molecules

The present invention further provides isolated nucleic acid molecules that encode a dehydrogenase polypeptide of the present invention. Such nucleic acid molecules will consist of, consist essentially of, or comprise a nucleotide sequence that encodes one of the dehydrogenase try polypeptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (patially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule. The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

Full-length genes may be cloned from known sequence using any one of a number of methods known in the art. For example, a method which employs XL-PCR (Perkin-Elmer, Foster City, Calif.) to amplify long pieces of DNA may be used. Other methods for obtaining full-length sequences are well known in the art.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life, or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the dehydrogenase polypeptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding, and stability of mRNA. In addition, the nucleic acid molecule may be fused to a marker sequence encoding, for example, a peptide that facilitates purification.

Isolated nucleic acid molecules can be in the form of RNA, such as mRNA, or in the form of DNA, including cDNA and genomic DNA obtained by cloning or produced by chemical synthetic techniques or by a combination thereof. The nucleic acid, especially DNA, can be double-straded or single-straded. Single-stranded nucleic acid can be the coding strand (sense strand) or the non-coding strand (anti-sense strand).

The invention further provides nucleic acid molecules that encode fragments of the peptides of the present invention and that encode obvious variants of the dehydrogenases of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or whole organisms. Accordingly, as discussed above, the variants can contain nucleotide substitutions, deletions inversions, and/or insertions. Variation can occur in either or both the coding and non-coding regions. The variations can produce both conservative and non-conservative amino acid substitutions.

The present invention further provides non-coding fragments of the nucleic acid molecules provided in the FIGS. 1 and 3. Preferred non-coding fragments include, but are not limited to, promoter sequences, enhancer sequences, gene modulating sequences, and gene termination sequences. Such fragments are useful in controlling heterologous gene expression and in developing screens to identify gene-modulating agents.

A fragment comprises a contiguous nucleotide sequence greater than 12 or more nucleotides. Further, a fragment could be at least 30, 40, 50, 100 250, or 500 nucleotides in length. The length of the fragment will be based on its intended use. For example, the fragment can encode epitope-bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50, or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence.

FIG. 3 provides information on SNPs that have been found in the gene encoding the transporter protein of the present invention. SNPs were identified at 11 different nucleotide positions in introns and regions 5' and 3' of the ORF. Such SNPs in introns and outside the ORF may affect control/regulatory elements. The changes in the amino acid sequence that these SNPs cause can readily be determined using the universal genetic code and the protein sequence provided in FIG. 2 as a base.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65° C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 11 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as those, which may encompass fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides. Moreover, the nucleic acid molecules are useful for constructing transgenic animals wherein a homolog of the nucleic acid molecule has been "knocked-out" of the animal's genome.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form, and distribution of nucleic acid expression. Experimental data as provided in FIG. 1 indicates that dehydrogenases of the present invention are expressed in the malignant melanoma (metastatic to lymph node), brain (glioblastoma), thyroid, colon tumor (RER+), stomach (poorly differentiated adenocarcinoma with signet ring cell features), primary Bells from tonsils, lung carcinoid, Burkitt lymphoma detected by a virtual northern blot. In addition, PCR-based tissue screening panel indicates expression in human leukocyte. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in dehydrogenase expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a dehydrogenase, such as by measuring a level of a receptor-encoding nucleic acid in a sample of cells from a subject e.g., mRNA or genomic DNA, or determining if a receptor gene has been mutated. Experimental data as provided in FIG. 1 indicates that dehydrogenases of the present invention are expressed in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma detected by a virtual northern blot. In addition, PCR-based tissue screening panel indicates expression in human leukocyte.

Nucleic acid expression assays are useful for drug screening to identify compounds that modulate dehydrogenase nucleic acid expression.

The invention thus provides a method for identifying a compound that can be used to treat a disorder associated with nucleic acid expression of the dehydrogenase gene, particularly biological and pathological processes that are mediated by the dehydrogenase in cells and tissues that express it. Experimental data as provided in FIG. 1 indicates expression in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma and human leukocyte. The method typically includes assaying the ability of the compound to modulate the expression of the dehydrogenase nucleic acid and thus identifying a compound that can be used to treat a disorder characterized by undesired dehydrogenase nucleic acid expression. The assays can be performed in cell-based and cell-free systems. Cell-based assays include cells naturally expressing the dehydrogenase nucleic acid or recombinant cells genetically engineered to express specific nucleic acid sequences.

The assay for dehydrogenase nucleic acid expression can involve direct assay of nucleic acid levels, such as mRNA levels, or on collateral compounds involved in the signal pathway. Further, the expression of genes that are up- or down-regulated in response to the dehydrogenase signal pathway can also be assayed. In this embodiment the regulatory regions of these genes can be operably linked to a reporter gene such as luciferase.

Thus, modulators of dehydrogenase gene expression can be identified in a method wherein a cell is contacted with a candidate compound and the expression of mRNA determined. The level of expression of dehydrogenase mRNA in the presence of the candidate compound is compared to the level of expression of dehydrogenase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate dehydrogenase nucleic acid expression in cells and tissues that express the dehydrogenase. Experimental data as provided in FIG. 1 indicates that dehydrogenases of the present invention are expressed in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma detected by a virtual northern blot. In addition, PCR-based tissue screening panel indicates expression in human leukocyte. Modulation includes both up-regulation (i.e. activation or agonization) or down-regulation (suppression or antagonization) of nucleic acid expression.

Alternatively, a modulator for dehydrogenase nucleic acid expression can be a small molecule or drug identified using the screening assays described herein as long as the drug or small molecule inhibits the dehydrogenase nucleic acid expression in the cells and tissues that express the protein. Experimental data as provided in FIG. 1 indicates expression in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma and human leukocyte.

The nucleic acid molecules are also useful for monitoring the effectiveness of modulating compounds on the expression or activity of the dehydrogenase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in dehydrogenase nucleic acid, and particularly in qualitative changes that lead to pathology. The nucleic acid molecules can be used to detect mutations in dehydrogenase genes and gene expression products such as mRNA. The nucleic acid molecules can be used as hybridization probes to detect naturally occurring genetic mutations in the dehydrogenase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns, or changes in gene copy number, such as amplification. Detection of a mutated form of the dehydrogenase gene associated with a dysfunction provides a diagnostic tool for an active disease or susceptibility to disease when the disease results from overexpression, underexpression, or altered expression of a dehydrogenase.

Individuals carrying mutations in the dehydrogenase gene can be detected at the nucleic acid level by a variety of techniques. FIG. 3 provides information on SNPs that have been found in the gene encoding the transporter protein of the present invention. SNPs were identified at 11 different nucleotide positions in introns and regions 5' and 3' of the ORF. Such SNPs in introns and outside the ORF may affect control/regulatory elements. The changes in the amino acid sequence that these SNPs cause can readily be determined using the universal genetic code and the protein sequence provided in FIG. 2 as a base. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077–1080 (1988); and Nakazawa et al., PNAS 91:360–364 (1994)), the latter of which can be particularly useful for detecting point mutations in the gene (see Abravaya et al., Nucleic Acids Res. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a dehydrogenase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant dehydrogenase gene and a wild-type gene can be determined by direct DNA sequencing. A variety of automated sequencing procedures can be utilized when performing the diagnostic assays (Naeve, C. W., Biotechniques 19:448 (1995)), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include, selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the dehydrogenase gene in an individual in order to select an appropriate compound or dosage regimen for treatment. FIG. 3 provides information on SNPs that have been found in the gene encoding the transporter protein of the present invention. SNPs were identified at 11 different nucleotide positions in introns and regions 5' and 3' of the ORF. Such SNPs in introns and outside the ORF may affect control/regulatory elements. The changes in the amnino acid sequence that these SNPs cause can readily be determined using the universal genetic code and the protein sequence provided in FIG. 2 as a base.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control dehydrogenase gene expression in cells, tissues, and organisms. A DNA antisense nucleic acid molecule is designed to be complementary to a region of the gene involved in transcription, preventing transcription and hence production of dehydrogenase. An antisense RNA or DNA nucleic acid molecule would hybridize to the mRNA and thus block translation of mRNA into dehydrogenase.

Alternatively, a class of antisense molecules can be used to inactivate mRNA in order to decrease expression of dehydrogenase nucleic acid. Accordingly, these molecules can treat a disorder characterized by abnormal or undesired dehydrogenase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the dehydrogenase, such as ligand binding.

The nucleic acid molecules also provide vectors for gene therapy in patients containing cells that are aberrant in dehydrogenase gene expression. Thus, recombinant cells, which include the patient's cells that have been engineered ex vivo and returned to the patient, are introduced into an individual where the cells produce the desired dehydrogenase to treat the individual.

The invention also encompasses kits for detecting the presence of a dehydrogenase nucleic acid in a biological sample. Experimental data as provided in FIG. 1 indicates that dehydrogenases of the present invention are expressed in the malignant melanoma (metastatic to lymph node), brain (glioblastoma), thyroid, colon tumor (RER+), stomach (poorly differentiated adenocarcinoma with signet ring cell features), primary B-cells from tonsils, lung carcinoid, Burkitt lymphoma detected by a virtual northern blot. In addition, PCR-based tissue screening panel indicates expression in human leukocyte. For example, the kit can comprise reagents such as a labeled or labelable nucleic acid or agent capable of detecting dehydrogenase nucleic acid in a biological sample; means for determining the amount of dehydrogenase nucleic acid in the sample; and means for comparing the amount of dehydrogenase nucleic acid in the sample with a standard. The compound or agent can be packaged in a suitable container. The kit can further comprise instructions for using the kit to detect dehydrogenase mRNA or DNA.

Nucleic Acid Arrays

The present invention further provides arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et. al., U.S. Pat. No. 5,807,522.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides that are only 7–20 nucleotides in length. The microarray may contain oligonucleotides that cover the known 5', or 3', sequence, sequential oligonucleotides that cover the full-length sequence; or unique oligonucleotides selected from particular areas along the length of the sequence. Polynucleotides used in the microarray may be oligonucleotides that are specific to a gene or genes of interest In order to produce oligonucleotides to a known sequence for a microarray, the gene(s) of interest (or an ORF identified from the contigs of the present invention) is typically examined using a computer algorithm that starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplfied in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of one or more of the proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention. FIG. 3 provides information on SNPs that have been found in the gene encoding the transporter protein of the present invention. SNPs were identified at 11 different nucleotide positions in introns and regions 5' and 3' of the ORF. Such SNPs in introns and outside the ORF may affect control/regulatory elements. The changes in the amnino acid sequence that these SNPs cause can readily be determined using the universal genetic code and the protein sequence provided in FIG. 2 as a base.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the human genome disclosed herein; and (b) one or more other containers comprising one or more of the following: wash reagents, reagents capable of detecting presence of a bound nucleic acid. Preferred kits will include chips that are capable of detecting the expression of 10 or more, 100 or more, or 500 or more, 1000 or more, or all of the genes expressed in Human.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified dehydrogenase genes of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterodehydrogenase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J*. 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol*. 3:2156–2165 (1983)) and the pVL series (Lucklow et al., *Virology* 170:31–39(1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J*. 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance, propagation, or expression of the nucleic acid molecules described herein. These are found for example in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd., Cold Spring Harbor Laboratory, Cold Spring Harbor Laboratory Press, Cold Spring Harbor, N.Y., 1989).

Host cells can contain more than one vector. Thus, different nucleotide sequences can be an introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced, or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell- free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a dehydrogenase polypeptide that can be further purified to produce desired amounts of dehydrogenase or fragments. Thus, host cells containing expression vectors are useful for peptide production.

Host cells are also useful for conducting cell-based assays involving the dehydrogenase or dehydrogenase fragments. Thus, a recombinant host cell expressing a native dehydrogenase is useful for assaying compounds that stimulate or inhibit dehydrogenase function.

Host cells are also useful for identifying dehydrogenase mutants in which these functions are affected. If the mutants naturally occur and give rise to a pathology, host cells containing the mutations are useful to assay compounds that have a desired effect on the mutant dehydrogenase (for example, stimulating or inhibiting function) which may not be indicated by their effect on the native dehydrogenase.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a dehydrogenase and identifying and evaluating modulators of dehydrogenase activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the dehydrogenase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the dehydrogenase to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355(1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813(1997) and PCT International Publication Nos. WO 97/07668 and WO 97/07669. In brief, a cell, e.g., a somatic cell, from the transgenic animal can be isolated and induced to exit the growth cycle and enter G$_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, dehydrogenase activation, and signal transduction, may not be evident from in vitro cell-free or cell-based assays. Accordingly, it is useful to provide non-human transgenic animals to assay in vivo dehydrogenase function, including ligand interaction, the effect of specific mutant dehydrogenases on dehydrogenase function and ligand interaction, and the effect of chimeric dehydrogenases. It is also possible to assess the effect of null mutations, which is mutations that substantially or completely eliminate one or more dehydrogenase functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

That which is claimed is:

1. An isolated polypeptide having an amino acid sequence consisting of SEQ ID NO:2.
2. An isolated polypeptide having an amino acid sequence comprising SEQ ID NO:2.
3. A composition comprising the polypeptide of claim 1 and a carrier.
4. A composition comprising the dehydrogenase of claim 2 and a carrier.
5. An isolated dehydrogenase consisting of an amino acid sequence having at least 95% sequence identity to SEQ ID NO:2.
6. A composition comprising the dehydrogenase of claim 5 and a carrier.
7. An isolated dehydrogenase comprising an amino acid sequence having at least 95% sequence identity to SEQ ID NO:2.
8. A composition comprising the dehydrogenase of claim 7 and a carrier.

* * * * *

SEQUENCE LISTING

<160> NUMBER OF SEQ ID NOS: 4

<210> SEQ ID NO 1
<211> LENGTH: 1335
<212> TYPE: DNA
<213> ORGANISM: Homo sapien

<400> SEQUENCE: 1

```
tgcttccgga gccggagggg gcccggcgta cccagccccc agcccgacgt gaccatgctg      60
tcccgcctcc taaaagaaca ccaggccaag cagaatgaac gcaaggagct gcaggaaaag     120
aggaggcgag aggctatcac tgcagcgacc tgcctgacag aagctttggt ggatcacctc     180
aatgtgggtg tggcccaggc ctacatgaac cagagaaagc tggaccatga ggtgaagacc     240
ctacaggtcc aggctgccca atttgccaag cagacaggcc agtggatcgg aatggtggag     300
aacttcaacc aggcactcaa gctggaccag agaggcttcc gagtcctggc cagctgcctg     360
accccctccg gggccgagga cctgcagcgg gtggcctcct cccgcctcca caccaccctg     420
ttggatatca ctgatcccca gagcgtccag caggcagcca agtgggtgga gatgcacgtt     480
aaggaagcag ggctttttgg tctggtgaat aatgctggtg tggctggtat catcggaccc     540
acaccatggc tgacccggga cgatttccag cgggtgctga atgtgaacac aatgggtccc     600 atcgggtca cccttgccct gctgcctctg ctgcagcaag cccggggccg ggtgatcaac     660
atcaccagcg tcctgggtcg cctggcagcc aatggtgggg gctactgtgt ctccaaattt     720
ggcctggagg ccttctctga cagcctgagg cgggatgtag ctcattttgg gatacgagtc     780
tccatcgtgg agcctggctt cttccgaacc cctgtgacca acctggagag tctggagaaa     840
accctgcagg cctgctgggc acggctgcct cctgccacac aggcccacta tgggggggcc     900
ttcctcacca agtacctgaa aatgcaacag cgcatcatga acctgatctg tgacccggac     960
ctaaccaagg tgagccgatg cctggagcat gccctgactg ctcgacaccc ccgaacccgc    1020
tacagcccag gttgggatgc caagctgctc tggctgcctg cctcctacct gccagccagc    1080
ctggtggatg ctgtgctcac ctgggtcctt cccaagcctg cccaagcagt ctactgaatc    1140
cagccttcca gcaagagatt gttttttcaag gacaaggact tgattttatt tctgccccca    1200
ccctggtact gcctggtgcc tgccacaaaa taagcactaa caaaagtgta ttgtttaaaa    1260
```

```
aataaaaaga aggtgggcag aaatgtgccc agtggaaaaa aaaaaaaaaa aaaaaaaaaa    1320
aaaaaaaaaa aaaaa                                                    1335
```

<210> SEQ ID NO 2
<211> LENGTH: 360
<212> TYPE: PRT
<213> ORGANISM: Homo sapien

<400> SEQUENCE: 2

```
Met Leu Ser Arg Leu Leu Lys Glu His Gln Ala Lys Gln Asn Glu Arg
 1               5                  10                  15

Lys Glu Leu Gln Glu Lys Arg Arg Glu Ala Ile Thr Ala Ala Thr
            20                  25                  30

Cys Leu Thr Glu Ala Leu Val Asp His Leu Asn Val Gly Val Ala Gln
            35                  40                  45

Ala Tyr Met Asn Gln Arg Lys Leu Asp His Glu Val Lys Thr Leu Gln
 50                  55                  60

Val Gln Ala Ala Gln Phe Ala Lys Gln Thr Gly Gln Trp Ile Gly Met
 65                  70                  75                  80

Val Glu Asn Phe Asn Gln Ala Leu Lys Leu Asp Gln Arg Gly Phe Arg
                 85                  90                  95

Val Leu Ala Ser Cys Leu Thr Pro Ser Gly Ala Glu Asp Leu Gln Arg
            100                 105                 110

Val Ala Ser Ser Arg Leu His Thr Thr Leu Leu Asp Ile Thr Asp Pro
            115                 120                 125

Gln Ser Val Gln Gln Ala Ala Lys Trp Val Glu Met His Val Lys Glu
    130                 135                 140

Ala Gly Leu Phe Gly Leu Val Asn Asn Ala Gly Val Ala Gly Ile Ile
145                 150                 155                 160

Gly Pro Thr Pro Trp Leu Thr Arg Asp Asp Phe Gln Arg Val Leu Asn
                165                 170                 175

Val Asn Thr Met Gly Pro Ile Gly Val Thr Leu Ala Leu Leu Pro Leu
            180                 185                 190

Leu Gln Gln Ala Arg Gly Arg Val Ile Asn Ile Thr Ser Val Leu Gly
        195                 200                 205

Arg Leu Ala Ala Asn Gly Gly Gly Tyr Cys Val Ser Lys Phe Gly Leu
    210                 215                 220

Glu Ala Phe Ser Asp Ser Leu Arg Arg Asp Val Ala His Phe Gly Ile
225                 230                 235                 240

Arg Val Ser Ile Val Glu Pro Gly Phe Phe Arg Thr Pro Val Thr Asn
                245                 250                 255

Leu Glu Ser Leu Glu Lys Thr Leu Gln Ala Cys Trp Ala Arg Leu Pro
            260                 265                 270

Pro Ala Thr Gln Ala His Tyr Gly Gly Ala Phe Leu Thr Lys Tyr Leu
        275                 280                 285

Lys Met Gln Gln Arg Ile Met Asn Leu Ile Cys Asp Pro Asp Leu Thr
    290                 295                 300

Lys Val Ser Arg Cys Leu Glu His Ala Leu Thr Ala Arg His Pro Arg
305                 310                 315                 320

Thr Arg Tyr Ser Pro Gly Trp Asp Ala Lys Leu Leu Trp Leu Pro Ala
                325                 330                 335

Ser Tyr Leu Pro Ala Ser Leu Val Asp Ala Val Leu Thr Trp Val Leu
            340                 345                 350
```

-continued

Pro Lys Pro Ala Gln Ala Val Tyr
    355                 360

<210> SEQ ID NO 3
<211> LENGTH: 19806
<212> TYPE: DNA
<213> ORGANISM: Homo sapien
<220> FEATURE:
<221> NAME/KEY: misc_feature
<222> LOCATION: (1)...(19806)
<223> OTHER INFORMATION: n = A,T,C or G

<400> SEQUENCE: 3

| | | | | | | |
|---|---|---|---|---|---|---|
| nnnnnnnnnn | nnnnnnnnnn | nnnattctat | ttaattagtc | tggaatcaag | gctttttttt | 60 |
| tttttttttt | gagacagagt | cccactctgt | cgcccgggct | ggagttcagt | ggcgtgatct | 120 |
| cggctcactg | caacctctgc | ctcccaggtt | caagcgattc | tcctgcctca | ggctcctgag | 180 |
| tagctgggat | tacaggcttg | tgccactacg | cctggctaaa | ttttgtattt | ttagtagata | 240 |
| caaggtttca | ccatgttggt | cagcctggtc | tcgaactcct | gacctcgtga | tccgcccgcc | 300 |
| tcggcctccc | aaagtgctgg | gattacgggc | gtgagccacc | gcacccggct | aatcacggca | 360 |
| ttttataag | ccttgtgatt | tctgtgattc | taatgtttag | attctaatgc | ttagccaggg | 420 |
| ttgagaacca | ccgatttaat | ccaatcccct | ctcctagttt | tactaaagag | aaaactataa | 480 |
| cctagaatgg | tgagcaactt | gcccaaagtc | acccaacatg | ttagtgcaag | gtgcaccgag | 540 |
| agagattgta | ccagtagcaa | gaatatgctc | atgatgttta | taattgttct | cgctggagtt | 600 |
| aatcccggaa | gcatttcttt | ttagttcaca | gaggccttat | ataaattact | ttttactttg | 660 |
| gcacagcact | tacgcttctg | ctaacactga | aatgggttcg | cattcctgac | cacaaaagga | 720 |
| cagagatgaa | attctacatt | cacacagccc | gccaagttag | ccaagctccc | taggaggctg | 780 |
| tctgaagtgc | ctaaaatgct | tctctacaat | gatcacccag | agctgagaga | cttcagtggg | 840 |
| gtagtgagaa | gaaagagggt | tgggagagac | aggaaagcat | cctctccttg | agggaaggaa | 900 |
| ctgggaatca | actgagaacc | agctagcact | gccaggaggt | gaggagaggg | aaggagaata | 960 |
| atttaaatga | ggccaggga | gcttctgctc | cctcaattaa | acgtgatag | acggcctgac | 1020 |
| accaccagcc | ctcgaagcct | gagatccaca | ggaaatgtta | aaaactggct | tggcaatata | 1080 |
| agtattagaa | aatacttctt | ccaacactca | ccaaaaacta | agctcccaat | aaagaacact | 1140 |
| tcacctgccc | tccgcaaccc | tctacctctc | ttccccgcca | agatcttcac | ccaaggtctc | 1200 |
| aagagggcgg | ttcccaacct | cacgtgacac | agcggtcacg | tgacatggcc | ccggggagcc | 1260 |
| gaggtgagcg | ttccagcttc | cggagccgga | gggggcccgg | cgtacccagc | ccccagcccg | 1320 |
| acgtgaccat | gctgtcccgc | ctcctaaaag | aacaccaggc | caagcagaat | gaacgcaagg | 1380 |
| agctgcaggg | tgagccaaat | atcctgtcgg | ccgttttctc | ttcggccgcg | gcctagcttc | 1440 |
| agcccggagc | ctggatctcg | agtaactaac | catatccagg | gaaagacgcc | agctagcggg | 1500 |
| caacgggcat | gggggnnnnn | nnnnnnnnnn | nnnnnnnnnn | nnnnnnnnnn | nnnnnnnnnn | 1560 |
| nnnnnnnnnn | nnnnnnnnnn | nnnnnnnnnn | nnnnnnnnnn | nnnnnnnnnn | nnnnnnnnnn | 1620 |
| nnnnnnnnnn | nnnnnnnnnn | nnnnnnnnnn | nnnnnnnnnn | nnnnnnnnnn | nnnnnnnnnn | 1680 |
| nnnnnnnnnn | nnnnnnnnnn | nnnnnnnnnn | nnnnnnnnnn | nnnnnnnnnn | nnnnnnnnnn | 1740 |
| nnnnnnnnnn | nnnnnnnnnn | nnnnnnnnnn | nnnnnnnnnn | nnnnnnnnnn | nnnnnnnnnn | 1800 |
| nnnnnnnnnn | nnnnnnnnnn | nnnnnnnnnn | nnnnnnnnnn | nnnnnnnnnn | nnnnnnnnnn | 1860 |
| nnnnnnnnnn | nnnnnnnnnn | nnnnnnnnnn | nnnnnnnnnn | nnnnnnnnnn | nnnnnnnnnn | 1920 |

-continued

| | |
|---|---|
| nnnnnnnnnn nnnnnnnnnn nnnnnnnnnn nnnnnnnnnn nnnnnnnnnn nnnnnnnnnn | 1980 |
| nnnnnnnnnn nnnnnnnnnn nnnnnnnnnn nnnnnnnnnn nnnnnnnnnn nnnnnnnnnn | 2040 |
| nnnnnnnnnn nnnnnnnnnn nnnnnnnnnn nnnnnnnnnn nnnnnnnnnn nnnnnnnnnn | 2100 |
| nnnnnnnnnn nnnnnnnnnn nnnnnnnnnn nnnnnnnnnn nnnnnnnnnn nnnnnnnnnn | 2160 |
| nnnnnnnnnn nnnnnnnnnn nnnnnnnnnn nnnnnnnnnn nnnnnnnnnn nnnnnnnnnn | 2220 |
| nnnnnnnnnn nnnnnnnnnn nnnnnnnnnn nnnnnnnnnn nnnnnnnnnn nnnnnnnnnn | 2280 |
| nnnnnnnnnn nnnnnnnnnn nnnnnnnnnn nnnnnnnnnn nnnnnnnnnn nnnnnnnnnn | 2340 |
| nnnnnnnnnn nnnnnnnnnn nnnnnnnnnn nnnnnnnnnn nnnnnnnnnn nnnnnnnnnn | 2400 |
| nnnnnnnnnn nnnnnnnnnn nnnnnnnnnn nnnnnnnnnn nnnnnnnnnn nnnnnnnnnn | 2460 |
| nnnnnnnnnn nnnnnnnnnn nnnnnnnnnn nnnnnnnnnn nnnnnnnnnn nnnnnnnnnn | 2520 |
| nnnnnnnnnn nnnnnnnnnn nnnnnnnnnn nnnnnnnnnn nnnnnnnnnn nnnnnnnnnn | 2580 |
| nnnnnnnnnn nnnnnnnnnn nnnnnnnnnn nnnnnnnnnn nnnnnnnnnn nnnnnnnnnn | 2640 |
| nnnnnnnnnn nnnnnnnnnn nnnnnnnnnn nnnnnnnnnn nnnnnnnnnn nnnnnnnnnn | 2700 |
| nnnnnnnnnn nnnnnnnnnn nnnnnnnnnn nnnnnnnnnn nnnnnnnnnn nnnnnnnnnn | 2760 |
| nnnnnnnnnn nnnnnnnnnn nnnnnnnnnn nnnnnnnnnn nnnnnnnnnn nnnnnnnnnn | 2820 |
| nnnnnnnnnn nnnnnnnnnn nnnnnnnnnn nnnnnnnnnn nnnnnnnnnn nnnnnnnnnn | 2880 |
| nnnnnnnnnn nnnnnnnnnn nnnnnnnnnn nnnnnnnnnn nnnnnnnnnn nnnnnnnnnn | 2940 |
| nnnnnnnnnn nnnnnnnnnn nnnnnnnnnn nnnnnnnnnn nnnnnnnnnn nnnnnnnnnn | 3000 |
| nnnnnnnnnn nnnnnnnnnn nnnnnnnnnn nnnnnnnnnn nnnnnnnnnn nnnnnnnnnn | 3060 |
| nnnnnnnnnn nnnnnnnnnn nnnnnnnnnn nnnnnnnnnn nnnnnnnnnn nnnnnnnnnn | 3120 |
| nnnnnnnnnn nnnnnnnnnn nnnnnnnnnn nnnnnnnnnn nnnnnnnnnn nnnnnnnnnn | 3180 |
| nnnnnnnnnn nnnnnnnnnn nnnnnnnnnn nnnnnnnnnn nnnnnnnnnn nnnnnnnnnn | 3240 |
| nnnnnnnnnn nnnnnnnnnn nnnnnnnnnn nnnnnnnnnn nnnnnnnnnn nnnnnnnnnn | 3300 |
| nnnnnnnnnn nnnnnnnnnn nnnnnnnnnn nnnnnnnnnn nnnnnnnnnn nnnnnnnnnn | 3360 |
| nnnnnnnnnn nnnnnnnnnn nnnnnnnnnn nnnnnnnnnn nnnnnnnnnn nnnnnnnnnn | 3420 |
| nnnnnnnnnn nnnnnnnnnn nnnnnnnnnn nnnnnnnnnn nnnnnnnnnn nnnnnnnnnn | 3480 |
| nnnnnnnnnn nnnnnnnnnn nnnnnnnnnn nntcccctcc aattcctttt ccccctctcc | 3540 |
| ccagcaaaat aggaggcgag aggctatcac tgcagcgacc tgcctgacag aagctttggt | 3600 |
| ggatcacctc aatgtggggt atggacctct tatcaacatc agtttcctcc ttccccaccc | 3660 |
| cgcccaagtt taggcactgg ccagtctggc cctcaaatag ctgttgaagg ggtgggatgt | 3720 |
| tccactaatt cccctatcct accccgcccc tcccagctct ttgtagagca acttgagtca | 3780 |
| actctgagtc ctagcactgg gcaagggagg aacagctgcc gtggttagag aagcagccag | 3840 |
| atttcccctt ccccacgtta acttccctgg catttacaac ttgatgccat ctgcccacct | 3900 |
| cccttcaccc ttccaagtcc agctgtcact tcagcaggag ggagagcacc ctccttcatt | 3960 |
| acagcttacc accctctcct ctgcctccca ccctctggca agcctgggga gcagctggca | 4020 |
| ggaaagagat ggcagagctg gtggtggtga gagtagaacc tgttccggga gctatggcag | 4080 |
| agccaggctg tctcttacct tcctattggg tctctaggga ccacccctg ccccagccct | 4140 |
| aaatgagaat gcaagtaaca gccaaagact tgggaaaaag caaagaacat tgtctcttga | 4200 |
| ccctaagtga cccagaagcg tgcagagatg atgatttgct agtctgccta ttggaagaaa | 4260 |
| ggcagtatgg taccttccac cccaggtcaa gtagaacagc tcggtgtgaa tccagagact | 4320 |

-continued

```
gagtcatcca agtgagccat gcaggggctg gggtcatctt tgttactcat cttgggggaa    4380
ggttgagaga agaaaagttg tggctggggc tctgatctc ccttctctcc aggcagctct     4440
ctttactcag tgtgaatata gaagcaggtg gtcaatgggg aaaaccagaa gttcaggaat    4500
tctcaggga gtctgtttca gttcctaccc gacccttgac agtgacccag ctgtctccca    4560
aaaagaagga acagggtctg ccctcccatt tcctccctcc cacattggca cctcctgggc    4620
tctgctgtgc ccatcatttg tgagattggc ccaggccttt ccctcttctt ttcctttgct    4680
agatgccacc ccactttcag cttagagggc agctaagcca aagccagatt agaaagggtt    4740
ttgtgttgct gcccacgcct cctctcattc cccggaaagg aaaacaaagg ctcagtctat    4800
cttggcccct gtcaggtgtc ctgcccactc cctcagcccc caccaacccc ttccccgctc    4860
cagcccccac acattccagt gggtgggggc accggatgtg gaatctcctg gctgagtaga    4920
gctctgggt gggaagtgaa aaattcaaca gccaataaag gagaacaatt attgcagggg     4980
ttggggaggg caaaaaacac tggcagaagg ttggggacac caaccccatg gtagtaatgg    5040
taaccacagc ccatacccttg attgaaaaga aaaactagtg cctaaggcag aaggagggga    5100
gagcatgtgt gtgtgtgtgt gtgtgtgttt gtgtgtgttc cttgatctgt gtgggcaaaa    5160
gcgaaggctt gggagagcaa ctgagagccg agaagaaacc cctgggatac cctcttttga    5220
cccagggttc ctgggaggg ggtttgtact cccatcctaa cccggcttca gggagggggcc   5280
caatttcccct ctccaacttc ttgcatagat ccctaggctt ccaatcactg ccagatgtgt    5340
tcctcctgct ggnnnnnnnn nnnnnnnnnn nnnnnnnnnn nnnnnnnnnn nnnnnnnnnn    5400
nnnnnnnnnn nnnnnnnnnn nnnnnnnnnn nnnnnnnnnn nnnnnnnnnn nnnnnnnnnc    5460
caggttttcc ctcccttccc ccactcagct gcaggaactc ctttttgggg tttggagctg    5520
gtatgtttct agtcagctcc gagcttggct ctcctgggaa tcctgggagt gaaaggaagg    5580
agctgggttt atttgcatgt actggtagtc atttgcatca catccaaaaa tggccaaaat    5640
tatgagccct gattcttggc tgaactccca ctgctgcaat ggaatattag tcccggagac    5700
cacccccaac tagctggagc tgatctcctc cctcctccaa ccccccagtg tggcccaggc    5760
ctacatgaac cagagaaagc tggaccatga ggtgaagacc ctacaggtcc aggctgccca    5820
atttgccaag cagacaggcc agtggatcgg aatggtggag aacttcaacc aggcactcaa    5880
ggtgggccat actccctacc tcaccacccc aatcctgggc cccattggc tgcctccagt     5940
caggttacct caggtttagg ttaaggagga agtagggtgg tccagaaaac ccatctata    6000
gccccagtgt cagaaaaggt agagaaagaa agaaaagcag ttggtgggtc caagtaaagc    6060
cttttccagg agatgaataa aacgtattcc ccagactgga agccatactc tacccattct    6120
gattcctggg ctcccacctc ctctcccct tcccaggaaa ttggggatgt ggagaactgg     6180
gctcggagca tcgagctgga catgcgcacc attgccactg cactggaata tgtctacaaa    6240
gggcagctgc agtctgcccc ttcctagccc ctgttccctc ccccaaccct atccctccta    6300
cctcacccgc agggggaagg agggaggctg acaagccttg aataaaacac aagcctccgt    6360
ttctctgtgg tgtgtttcag agagctacta gctccagtgt cggggtggg agtggaaggt     6420
tcaaaggtgg tttccctgag ggacaggtac cttttgggga gagggtggaa ctagcttcct    6480
cttactatcc caactctctt ctcctccatg gcccttgtgc aggtgtctgt taggcaagca    6540
gagggtggga gttcccatcc ctcctgagag aaggtcctag tagccctgcc ccaagcttcc    6600
taattcagga cttgtttcct acagaagaga aacaaggcaa ggtacaggcc tggtccccag    6660
```

```
ctctggcttt ctgcctctcc acgtgctcat ggcctctccc aggctaactc taagcagtgt    6720
catgagtctg agccaggtgg gagattaatt cctgggggca cttcagggct gagaaggggg    6780
aggaatgaca ggtccagtaa ccgttaccaa cagagcagtg cagctgccat ccttgacagc    6840
tccctcctcc ttggagacca tgacatagat ggtcaggaac ccaggctgag aaagacagcc    6900 aagggtggg gggagcctag gcaaatctgg cctctgccaa gtcctggctt cagccaggca    6960
agctccagcc tccctggctc ctcctcctcc tcagtcctat ccccaccctg tcacacatac    7020
acttaatacg cctggcatcc aagtccaccc actccggact ttggccttag cagtagttag    7080
tgtgggaggc tgggaagact gggagcagtc tcttaaacaa aagcaaaaga ataagcttcg    7140
ggcgctgtag tacctgccag ctttcgccac aggaggtaag tggatactgg gagctggggg    7200
aactgagaag actagccaga tattacatgt attgccaact caaaactttc agcttttaac    7260
atgcttcctc acacattatc ccctttgatc ctccacaact ctgaggtgga cctggtgggt    7320
cttagcccca cttggtagat gagaaaatag gttgagagag acagtgagat gctcagtatc    7380
acacagcaaa cctcttggcc ctatacatca ttccaaacac aagacccagg ttgcatatag    7440
aaggttcagt gtccctggtt tagaaggaga ggtggtgtga ggcaagcaag aagatgcctc    7500
tgctgcactc cagcctgggc gacagagtga gactccatct caaaaaaaaa aaaaaaaaa    7560 aaaagatgcc tctgctccat acagcaggtc tgtacacagg atctggctca tgtggtttta    7620
gttnnnnnnn nnnnnnnnnn nnnnnnnnnn nnnnnnnnnn nnnnnnnnnn nnnnnnnnnn    7680
nnnnnnnnnn nnnnnnnnnn tggttttagt taaagttagc cacaaataca gcgtctgccc    7740
acatctttgc tttgaacaga tgagccatgg ttggccaatt atctgccaac cagataattt    7800
ctcaatatgc tcacaccaga tgcttccagc tagggagggt attaggggaa agggcttgag    7860
ggccacagta aactggacaa gttttttctgc ccagcctagg ctgccacctg taggtcactt    7920
gggctccagc tatgtggctg cctcttctgc tgggtgcctt actctgggca gtgctgtggt    7980
tgctcaggga ccggcagagc ctgcccgcca gcaatgcctt tgtcttcatc accggctgtg    8040
actcaggctt tgggcgcctt ctggcactgc agctggacca gagaggcttc cgagtcctgg    8100
ccagctgcct gaccccctcc ggggccgagg acctgcagcg ggtggcctcc tcccgcctcc    8160
acaccaccct gttggatatc actgatcccc agagcgtcca gcaggcagcc aagtgggtgg    8220
agatgcacgt taaggaagca ggtaagtatg gtagaccacc aggaatatgg tgtggggtgt    8280
cctgatcccc acagtcaccc caggagtcac ctgcaagggc tgtggtaagc taaagggaca    8340
atttgaggag aagcagtttt cagatgctcc caggaagaag agggagctgt gggagtgcct    8400
cacctacccc cagcatcctt ttcatctccc cacagggctt tttggtctgg tgaataatgc    8460
tggtgtggct ggtatcatcg gacccacacc atggctgacc cggacgatt tccagcgggt    8520 gctgaatgtg aacacaatgg gtcccattgg ggtcacccct tgcctgctgc ctctgctgca    8580
gcaagcccgg ggccgggtga tcaacatcac cagcgtcctg ggtcgcctgg cagccaatgg    8640
tgggggctac tgtgtctcca aatttggcct ggaggccttc tctgacagcc tgaggtgagg    8700
ggtacagggc tctgggttcc aggactaaca gcagcccact caacaaacgt gggccagcag    8760
aggtggttaa aatacagcac attggaatag ttaaaagag acagtttagg gctaaacttc    8820
atgggttcaa tgaagtctac ccttatgtaa gctttgtgac nnnnnnnnnn nnnnnnnnnn    8880
nnnnnnnnnn nnnnnnnnnn nnnnnnnnnn nnnnnnnnnn nnnnnnnnnn nnnnnnnnnn    8940
nnnnnnnnnn nnnnnnnnnn nnnnnnnnnn nnnnnnnnnn nnnnnnnnnn nnnnnnnnnn    9000
nnnnnnnnnn nnnnnnnnnn nnnnnnnnnn nnnnnnnnnn nnnnnnnnnn nnnnnnnnnn    9060
```

| | |
|---|---|
| nnnnnnnnnn nnnnnnnnnn nnnnnnnnnn nnnnnnnnnn nnnnnnnnnn nnnnnnnnnn | 9120 |
| nnnnnnnnnn nnnnnnnnnn nnnnnnnnnn nnnnnnnnnn nnnnnnnnnn nnnnnnnnnn | 9180 |
| nnnnnnnnnn nnnnnnnnnn nnnnnnnnnn nnnnnnnnnn nnnnnnnnnn nnnnnnnnnn | 9240 |
| nnnnnnnnnn nnnnnnnnnn nnnnnnnnnn nnnnnnnnnn nnnnnnnnnn nnnnnnnnnn | 9300 |
| nnnnnnnnnn nnnnnnnnnn nnnnnnnnnn nnnnnnnnnn nnnnnnnnnn nnnnnnnnnn | 9360 |
| nnnnnnnnnn nnnnnnnnnn nnnnnnnnnn nnnnnnnnnn nnnnnnnnnn nnnnnnnnnn | 9420 |
| nnnnnnnnnn nnnnnnnnnn nnnnnnnnnn nnnnnnnnnn nnnnnnnnnn nnnnnnnnnn | 9480 |
| nnnnnnnnnn nnnnnnnnnn nnnnnnnnnn nnnnnnnnnn nnnnnnnnnn nnnnnnnnnn | 9540 |
| nnnnnnnnnn nnnnnnnnnn nnnnnnnnnn nnnnnnnnnn nnnnnnnnnn nnnnnnnnnn | 9600 |
| nnnnnnnnnn nnnnnnnnnn nnnnnnnnnn nnnnnnnnnn nnnnnnnnnn nnnnnnnnnn | 9660 |
| nnnnnnnnnn nnnnnnnnnn nnnnnnnnnn nnnnnnnnnn nnnnnnnnnn nnnnnnnnnn | 9720 |
| nnnnnnnnnn nnnnnnnnnn nnnnnnnnnn nnnnnnnnnn nnnnnnnnnn nnnnnnnnnn | 9780 |
| nnnnnnnnnn nnnnnnnnnn nnnnnnnnnn nnnnnnnnnn nnnnnnnnnn nnnnnnnnnn | 9840 |
| nnnnnnnnnn nnnnnnnnnn nnnnnnnnnn nnnnnnnnnn nnnnnnnnnn nnnnnnnnnn | 9900 |
| nnnnnnnnnn nnnnnnnnnn nnnnnnnnnn nnnnnnnnnn nnnnnnnnnn nnnnnnnnnn | 9960 |
| nnnnnnnnnn nnnnnnnnnn nnnnnnnnnn nnnnnnnnnn nnnnnnnnnn nnnnnnnnnn | 10020 |
| nnnnnnnnnn nnnnnnnnnn nnnnnnnnnn nnnnnnnnnn nnnnnnnnnn nnnnnnnnnn | 10080 |
| nnnnnnnnnn nnnnnnnnnn nnnnnnnnnn nnnnnnnnnn nnnnnnnnnn nnnnnnnnnn | 10140 |
| nnnnnnnnnn nnnnnnnnnn nnnnnnnnnn nnnnnnnnnn nnnnnnnnnn nnnnnnnnnn | 10200 |
| nnnnnnnnnn nnnnnnnnnn nnnnnnnnnn nnnnnnnnnn nnnnnnnnnn nnnnnnnnnn | 10260 |
| nnnnnnnnnn nnnnnnnnnn nnnnnnnnnn nnnnnnnnnn nnnnnnnnnn nnnnnnnnnn | 10320 |
| nnnnnnnnnn nnnnnnnnnn nnnnnnnnnn nnnnnnnnnn nnnnnnnnnn nnnnnnnnnn | 10380 |
| nnnnnnnnnn nnnnnnnnnn nnnnnnnnnn nnnnnnnnnn nnnnnnnnnn nnnnnnnnnn | 10440 |
| nnnnnnnnnn nnnnnnnnnn nnnnnnnnnn nnnnnnnnnn nnnnnnnnnn nnnnnnnnnn | 10500 |
| nnnnnnnnnn nnnnnnnnnn nnnnnnnnnn nnnnnnnnnn nnnnnnnnnn nnnnnnnnnn | 10560 |
| nnnnnnnnnn nnnnnnnnnn nnnnnnnnnn nnnnnnnnnn nnnnnnnnnn nnnnnnnnnn | 10620 |
| nnnnnnnnnn nnnnnnnnnn nnnnnnnnnn nnnnnnnnnn nnnnnnnnnn nnnnnnnnnn | 10680 |
| nnnnnnnnnn nnnnnnnnnn nnnnnnnnnn nnnnnnnnnn nnnnnnnnnn nnnnnnnnnn | 10740 |
| nnnnnnnnnn nnnnnnnnnn nnnnnnnnnn nnnnnnnnnn nnnnnnnnnn nnnnnnnnnn | 10800 |
| nnnnnnnnnn nnnnnnnnnn nnnnnnnnnn nnnnnnnnnn nnnnnnnnnn nnnnnnnnnn | 10860 |
| nnnnnnnnnn nnnnnnnnnn nnnnnnnnnn nnnnnnnnnn nnnnnnnnnn nnnnnnnnnn | 10920 |
| nnnnnnnnnn nnnnnnnnnn nnnnnnnnnn nnnnnnnnnn nnnnnnnnnn nnnnnnnnnn | 10980 |
| nnnnnnnnnn nnnnnnnnnn nnnnnnnnnn nnnnnnnnnn nnnnnnnnnn nnnnnnnnnn | 11040 |
| nnnnnnnnnn nnnnnnnnnn nnnnnnnnnn nnnnnnnnnn nnnnnnnnnn nnnnnnnnnn | 11100 |
| nnnnnnnnnn nnnnnnnnnn nnnnnnnnnn nnnnnnnnnn nnnnnnnnnn nnnnnnnnnn | 11160 |
| nnnnnnnnnn nnnnnnnnnn nnnnnnnnnn nnnnnnnnnn nnnnnnnnnn nnnnnnnnnn | 11220 |
| nnnnnnnnnn nnnnnnnnnn nnnnnnnnnn nnnnnnnnnn nnnnnnnnnn nnnnnnnnnn | 11280 |
| nnnnnnnnnn nnnnnnnnnn nnnnnnnnnn nnnnnnnnnn nnnnnnnnnn nnnnnnnnnn | 11340 |
| nnnnnnnnnn nnnnnnnnnn nnnnnnnnnn nnnnnnnnnn nnnnnnnnnn nnnnnnnnnn | 11400 |

```
nnnnnnnnnn nnnnnnnnnn nnnnnnnnnn nnnnnnnnnn nnnnnnnnnn nnnnnnnnnn    11460
nnnnnnnnnn nnnnnnnnnn nnnnnnnnnn nnnnnnnnnn nnnnnnnnnn nnnnnnnnnn    11520
nnnnnnnnnn nnnnnnnnnn nnnnnnnnnn nnnnnnnnnn nnnnnnnnnn nnnnnnnnnn    11580
nnnnnnnnnn nnnnnnnnnn nnnnnnnnnn nnnnnnnnnn nnnnnnnnnn nnnnnnnnnn    11640
nnnnnnnnnn nnnnnnnnnn nnnnnnnnnn nnnnnnnnnn nnnnnnnnnn nnnnnnnnnn    11700
nnnnnnnnnn nnnnnnnnnn nnnnnnnnnn nnnnnnnnnn nnnnnnnnnn nnnnnnnnnn    11760
nnnnnnnnnn nnnnnnnnnn nnnnnnnnnn nnnnnnnnnn nnnnnnnnnn nnnnnnnnnn    11820
nnnnnnnnnn nnnnnnnnnn nnnnnnnnnn nnnnnnnnnn nnnnnnnnnn nnnnnnnnnn    11880
nnnnnnnnnn nnnnnnnnnn nnnnnnnnnn nnnnnnnnnn nnnnnnnnnn nnnnnnnnnn    11940
nnnnnnnnnn nnnnnnnnnn nnnnnnnnnn nnnnnnnnnn nnnnnnnnnn nnnnnnnnnn    12000
nnnnnnnnnn nnnnnnnnnn nnnnnnnnnn nnnnnnnnnn nnnnnnnnnn nnnnnnnnnn    12060
nnnnnnnnnn nnnnnnnnnn nnnnnnnnnn nnnnnnnnnn nnnnnnnnnn nnnnnnnnnn    12120
nnnnnnnnnn nnnnnnnnnn nnnnnnnnnn nnnnnnnnnn nnnnnnnnnn nnnnnnnnnn    12180
nnnnnnnnnn nnnnnnnnnn nnnnnnnnnn nnnnnnnnnn nnnnnnnnnn nnnnnnnnnn    12240
nnnnnnnnnn nnnnnnnnnn nnnnnnnnnn nnnnnnnnnn nnnnnnnnnn nnnnnnnnnn    12300
nnnnnnnnnn nnnnnnnnnn nnnnnnnnnn nnnnnnnnnn nnnnnnnnnn nnnnnnnnnn    12360
nnnnnnnnnn nnnnnnnnnn nnnnnnnnnn nnnnnnnnnn nnnnnnnnnn nnnnnnnnnn    12420
nnnnnnnnnn nnnnnnnnnn nnnnnnnnnn nnnnnnnnnn nnnnnnnnnn nnnnnnnnnn    12480
nnnnnnnnnn nnnnnnnnnn nnnnnnnnnn nnnnnnnnnn nnnnnnnnnn nnnnnnnnnn    12540
nnnnnnnnnn nnnnnnnnnn nnnnnnnnnn nnnnnnnnnn nnnnnnnnnn nnnnnnnnnn    12600
nnnnnnnnnn nnnnnnnnnn nnnnnnnnnn nnnnnnnnnn nnnnnnnnnn nnnnnnnnnn    12660
nnnnnnnnnn nnnnnnnnnn nnnnnnnnnn nnnnnnnnnn nnnnnnnnnn nnnnnnnnnn    12720
nnnnnnnnnn nnnnnnnnnn nnnnnnnnnn nnnnnnnnnn nnnnnnnnnn nnnnnnnnnn    12780
nnnnnnnnnn nnnnnnnnnn nnnnnnnnnn nnnnnnnnnn nnnnnnnnnn nnnnnnnnnn    12840
nnnnnnnnnn nnnnnnnnnn nnnnnnnnnn nnnnnnnnnn nnnnnnnnnn nnnnnnnnnn    12900
nnnnnnnnnn nnnnnnnnnn nnnnnnnnnn nnnnnnnnnn nnnnnnnnnn nnnnnnnnnn    12960
nnnnnnnnnn nnnnnnnnnn nnnnnnnnnn nnnnnnnnnn nnnnnnnnnn nnnnnnnnnn    13020
nnnnnnnnnn nnnnnnnnnn nnnnnnnnnn nnnnnnnnnn nnnnnnnnnn nnnnnnnnnn    13080
nnnnnnnnnn nnnnnnnnnn nnnnnnnnnn nnnnnnnnnn nnnnnnnnnn nnnnnnnnnn    13140
nnnnnnnnnn nnnnnnnnnn nnnnnnnnnn nnnnnnnnnn nnnnnnnnnn nnnnnnnnnn    13200
nnnnnnnnnn nnnnnnnnnn nnnnnnnnnn nnnnnnnnnn nnnnnnnnnn nnnnnnnnnn    13260
nnnnnnnnnn nnnnnnnnnn nnnnnnnnnn nnnnnnnnnn nnnnnnnnnn nnnnnnnnnn    13320
nnnnnnnnnn nnnnnnnnnn nnnnnnnnnn nnnnnnnnnn nnnnnnnnnn nnnnnnnnnn    13380
nnnnnnnnnn nnnnnnnnnn nnnnnnnnnn nnnnnnnnnn nnnnnnnnnn nnnnnnnnnn    13440
nnnnnnnnnn nnnnnnnnnn nnnnnnnnnn nnnnnnnnnn nnnnnnnnnn nnnnnnnnnn    13500
nnnnnnnnnn nnnnnnnnnn nnnnnnnnnn nnnnnnnnnn nnnnnnnnnn nnnnnnnnnn    13560
nnnnnnnnnn nnnnnnnnnn nnnnnnnnnn nnnnnnnnnn nnnnnnnnnn nnnnnnnnnn    13620
nnnnnnnnnn nnnnnnnnnn nnnnnnnnnn nnnnnnnnnn nnnnnnnnnn nnnnnnnnnn    13680
nnnnnnnnnn nnnnnnnnnn nnnnnnnnnn nnnnnnnnnn nnnnnnnnnn nnnnnnnnnn    13740
nnnnnnnnnn nnnnnnnnnn nnnnnnnnnn nnnnnnnnnn nnnnnnnnnn nnnnnnnnnn    13800
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 13860 |
| nnnnnnnnnn | nnnnnnnnnn | nnnnnnnnnn | nnnnnnnnnn | nnnnnnnnnn | nnnnnnnnnn | 13920 |
| nnnnnnnnnn | nnnnnnnnnn | nnnnnnnnnn | nnnnnnnnnn | nnnnnnnnnn | nnnnnnnnnn | 13980 |
| nnnnnnnnnn | nnnnnnnnnn | nnnnnnnnnn | nnnnnnnnnn | nnnnnnnnnn | nnnnnnnnnn | 14040 |
| nnnnnnnnnn | nnnnnnnnnn | nnnnnnnnnn | nnnnnnnnnn | nnnnnnnnnn | nnnnnnnnnn | 14100 |
| nnnnnnnnnn | nnnnnnnnnn | nnnnnnnnnn | nnnnnnnnnn | nnnnnnnnnn | nnnnnnnnnn | 14160 |
| nnnnnnnnnn | nnnnnnnnnn | nnnnnnnnnn | nnnnnnnnnn | nnnnnnnnnn | nnnnnnnnnn | 14220 |
| nnnnnnnnnn | nnnnnnnnnn | nnnnnnnnnn | nnnnnnnnnn | nnnnnnnnnn | nnnnnnnnnn | 14280 |
| nnnnnnnnnn | nnnnnnnnnn | nnnnnnnnnn | nnnnnnnnnn | nnnnnnnnnn | nnnnnnnnnn | 14340 |
| nnnnnnnnnn | nnnnnnnnnn | nnnnnnnnnn | nnnnnnnnnn | ttcttagcag | gagtataagg | 14400 |
| nnnnnnnnnn | nnnnnnnnnn | nnnnnnnnnn | nnnnnnnnnn | nnnnnnnnnn | nnnnnnnnnn | 14460 |
| nnnnnnnnnn | nnnnnnnnnn | nnnnnnnnnn | nnnnnnnnnn | nnnnnnnnnn | nnnnnnnnnn | 14520 |
| nnnnnnnnnn | nnnnnnnnnn | nnnnnnnnnn | nnnnnnnnnn | nnnnnnnnnn | nnnnnnnnnn | 14580 |
| nnnnnnnnnn | nnnnnnnnnn | nnnnnnnnnn | nnnnnnnnnn | nnnnnnnnnn | nnnnnnnnnn | 14640 |
| nnnnnnnnnn | nnnnnnnnnn | nnnnnnnnnn | nnnnnnnnnn | nnnnnnnnnn | nnnnnnnnnn | 14700 |
| nnnnnnnnnn | nnnnnnnnnn | nnnnnnnnnn | nnnnnnnnnn | nnnnnnnnnn | nnnnnnnnnn | 14760 |
| nnnnnnnnnn | nnnnnnnnnn | nnnnnnnnnn | nnnnnnnnnn | nnnnnnnnnn | nnnnnnnnnn | 14820 |
| nnnnnnnnnn | nnnnnnnnnn | nnnnnnnnnn | nnnnnnnnnn | nnnnnnnnnn | nnnnnnnnnn | 14880 |
| nnnnnnnnnn | nnnnnnnnnn | nnnnnnnnnn | nnnnnnnnnn | nnnnnnnnnn | nnnnnnnnnn | 14940 |
| nnnnnnnnnn | nnnnnnnnnn | nnnnnnnnnn | nnnnnnnnnn | nnnnnnnnnn | nnnnnnnnnn | 15000 |
| nnnnnnnnnn | nnnnnnnnnn | nnnnnnnnnn | nnnnnnnnnn | nnnnnnnnnn | nnnnnnnnnn | 15060 |
| nnnnnnnnnn | nnnnnnnnnn | nnnnnnnnnn | nnnnnnnnnn | nnnnnnnnnn | nnnnnnnnnn | 15120 |
| nnnnnnnnnn | nnnnnnnnnn | nnnnnnnnnn | nnnnnnnnnn | nnnnnnnnnn | nnnnnnnnnn | 15180 |
| nnnnnnnnnn | nnnnnnnnnn | nnnnnnnnnn | nnnnnnnnnn | nnnnnnnnnn | nnnnnnnnnn | 15240 |
| nnnnnnnnnn | nnnnnnnnnn | nnnnnnnnnn | nnnnnnnnnn | nnnnnnnnnn | nnnnnnnnnn | 15300 |
| nnnnnnnnnn | nnnnnnnnnn | nnnnnnnnnn | nnnnnnnnnn | nnnnnnnnnn | nnnnnnnnnn | 15360 |
| nnnnnnnnnn | nnnnnnnnnn | nnnnnnnnnn | nnnnnnnnnn | nnnnnnnnnn | nnnnnnnnnn | 15420 |
| nnnnnnnnnn | nnnnnnnnnn | nnnnnnnnnn | nnnnnnnnnn | nnnnnnnnnn | nnnnnnnnnn | 15480 |
| nnnnnnnnnn | nnnnnnnnnn | nnnnnnnnnn | nnnnnnnnnn | nnnnnnnnnn | nnnnnnnnnn | 15540 |
| nnnnnnnnnn | nnnnnnnnnn | nnnnnnnnnn | nnnnnnnnnn | nnnnnnnnnn | nnnnnnnnnn | 15600 |
| nnnnnnnnnn | nnnnnnnnnn | nnnnnnnnnn | nnnnnnnnnn | nnnnnnnnnn | nnnnnnnnnn | 15660 |
| nnnnnnnnnn | nnnnnnnnnn | nnnnnnnnnn | nnnnnnnnnn | nnnnnnnnnn | nnnnnnnnnn | 15720 |
| nnnnnnnnnn | nnnnnnnnnn | nnnnnnnnnn | nnnnnnnnnn | nnnnnnnnnn | nnnnnnnnnn | 15780 |
| nnnnnnnnnn | nnnnnnnnnn | nnnnnnnnnn | nnnnnnnnnn | nnnnnnnnnn | nnnnnnnnnn | 15840 |
| nnnnnnnnnn | nnnnnnnnnn | nnnnnnnnnn | nnnnnnnnnn | nnnnnnnnnn | nnnnnnnnnn | 15900 |
| nnnnnnnnnn | nnnnnnnnnn | nnnnnnnnnn | nnnnnnnnnn | nnnnnnnnnn | nnnnnnnnnn | 15960 |
| nnnnnnnnnn | nnnnnnnnnn | nnnnnnnnnn | ttcttagcag | gagtataagg | cgcctaagct | 16020 |
| tagtctacct | tttaaggaag | cctgcgtttg | tcaccatcac | tcagcaaata | acctgaatgt | 16080 |
| ctcctgtctc | tcagccttaa | ttttcaggc | agcatcatgg | gacacatact | tttagttttg | 16140 |

-continued

```
agacaaggcc ttgctctcac ccagggtgga gtgcagtggt gcagtcacgg cccactgaac   16200
ttcaaactcc taggctcaag cagctcaagc gatatccgcc tcagcctcct gagtagctga   16260
gaccacaggc gcgtgccagc atgcctggct agtattttt tacagatggg gtcttgctgt    16320
ggtgaccaga cttgtctcaa actcccggcc tcaagcgatg cttccgcctg ggcctcccaa   16380
agtgttggga ttataggtgt gagccactgc atactggaac acatacttta tacttgaatt   16440 ttttttatc cccttccctc ctgctcctta cctatacttg gatttctaca tctgtgccag    16500
ggcagtggga tgtatcccca cttccccat cagcttaccc tccagcaaat acgagactat    16560 accctcaat atccagcact cagggctcaa ccatgtgttt tgggagcaag ggaatggggt    16620
tcctctaggt caggaatcgg caaactcagt actcaagcca gatctggcca gctgcctaca   16680
agctgataat ggttttttt attttaaat ggttacattg taaactgtta tataagtacc     16740
tgataatatc attaattttg tttcttggcc tgccatgctt aaaatattaa ctctctggcc   16800
ctttaagaaa aaacgtgct gaccctgct ctagatcaaa gaaacaaac ctcaaaaata     16860 cttcctccc tctaccccac ttgacccttg tcccggggca gtaggcatct ccgtcaaaac    16920
tcttgtccct ggtctgtggt aactttctca gctccccaac ccatgtccct caaagtcccc   16980
tccctatagg gcaagaaccc agcaacttcg ctctgccccg actctaggcg ggatgtagct   17040 catttttggga tacgagtctc catcgtggag cctggcttct tccgaacccc tgtgaccaac   17100
ctggagagtc tggagaaaac cctgcaggcc tgctgggcac ggctgcctcc tgccacacag   17160
gcccactatg ggggggcctt cctcaccaag tgtgagtagc caggcccaca caggggcaca   17220
tgaagggaaa caagtaccag aaaggccagt cctgcataag cctgctagga ggtgggtggg   17280
gcacccaggg cagggttgag ggtgaacagg atgttacaan agtgcccagg ccatgtggaa   17340 cctcccact ccccacactg aggaggggac tgagggtgac aagcccaggg ccccagaaga   17400
cagtacctaa gatgggctgg agtgaggaag ggaaactgat tgcaaccacc tatgggctg    17460 cagacctgaa aatgcaacag cgcatcatga acctgatctg tgacccggac ctaaccaagg   17520
tgagccgatg cctggagcat gccctgactg ctcgacaccc ccgaacccgc tacagcccag   17580
gttgggatgc caagctgctc tggctgcctg cctcctacct gccagccagc ctggtggatg   17640
ctgtgctcac ctgggtcctt cccaagcctg cccaagcagt ctactgaatc cagccttcca   17700
gcaagagatt gtttttcaag gacaaggact ttgatttatt tctgccccca ccctggtact   17760
gcctggtgcc tgccacaaaa taagcactaa caaaagtgta ttgtttaaaa aataaaaaga   17820
aggtgggcag aaatgtgccc agtggaaggc tgaccccatt taagtgccaa ctactccaaa   17880
ccgacatgct cacggtctct ggcctgttca gtccctgcaa aacagctagc acccacagtg   17940
gggcgccagg gaactgcctc acatctacag ctgcacgtcg gggagtggcc atcaaagggc   18000
actttaatac atttcccta ttttctgaag gggagtaagg ttgcaattca gtgtctgtac    18060
tgggaatggt cttcatattt cttggggggag aagagcaggt gatgagggtt ctgggccagg   18120
ctgggtggct tccatggaag aaaaggcaat attcacataa attctcctgc taaggacact   18180
gaccacacag gtgtcaaggc aacttatcat acttcgaaag gagctggatc ccttgaggat   18240
tggccaggaa gggaggtgct gggcccttag cggtgcacag aaggccagga agatgtccaa   18300
ggcagatggg ggctgggctc tcgcaggtgg gacctttctg gggagctgct ttgacttatg   18360
cagcagatgg cttcatgaat gttcatagtg agcctggcag cataagacta gggggcagaa   18420
agcaccacag tctctggatc ctcacttctc ccactgcctg cccaaccaac accttcgcaa   18480
agtcctcctt tcccaaacac ccccccaaaat agacctcgaa gtacacatgc attaaggtcc   18540
```

-continued

```
cagaggacag ggaacatcag taaggaaagg aaggaatcaa gcatcactct aagacaaact    18600
cagaccatct cttttcggtc tgaaaaaata atccgtttaa ttgaaaaacc tggaggatac    18660
tattccactc ccccagatga ggaggctgag gagaccagac ccctacatca cctcgtagcc    18720
acttctgata ctcttcacga ggcagcaggc aaagacaatt cccaaaacct agaaggaaag    18780
atggggacag gggtggagag gagtcagaag ggctagctac ctcagaccca tgcaagagac    18840
tccaaacaca cactcccagg ccagtacctc ctgttcagca ccctcctccc ctcagccccc    18900
ttccctccag gcaaccctgg acagagtccc agccctgct cagggttatc tcttacctcg     18960
acaaaagcaa ttccaagggc tgctgcagct accaccagca cattttcct cagccagccc    19020 ccaatcttct ccacacagcc ctgaaggtgg caggcacaaa ggacaaaagc accatcagaa    19080
acttcccacc ccaaccccct cccttggtcc atcagtctct tccctgcccc tgtacctttc    19140
accccaccct tagcatttcc agatcccctc cccatccctg accctgtcca cctccatcct    19200
gggtctcttg cattctaaaa catttcccag gtttcccaag tccatacac agtctcctcc      19260 ctacctcctt atggatcgcc ttctcgttga aattaatccc acagcccaca gtaacattaa    19320
tgcagcagga gtcggggact cggttcttcg acatggaagg gattttctcc caatctgtgt    19380
agttagcagc cccacagcac ttaaactggg ggagggaaga aatatggaga agaaggttgt    19440
taagtgaacc ttcaccttca atatggagat gagaattctt tttttttttt ttttttttt     19500 tttgagacag agacttgctc tgttgcccag acaagtgccc agcggtggct caatctcggc    19560
tcactgcaac ctccgcctcc cgggttcaag cgattctcct gcctcaccct cctgagtagg    19620
tgggattaca ggcactcacc accacacctg gctaattttt gtattttag tagagacagg     19680 gtttcaccac gttggccagg ctagtcttga acttctgacc tcaggtgatc tgcccacctc    19740
ggccttcaaa agtgctgaga ttacaggcgt gagtcaccac acccagcctt ggagatgaga    19800
attctc                                                               19806
```

<210> SEQ ID NO 4
<211> LENGTH: 274
<212> TYPE: PRT
<213> ORGANISM: Homo sapien

<400> SEQUENCE: 4

```
Ala Leu Gln Leu Asp Gln Arg Gly Phe Arg Val Leu Ala Ser Cys Leu
  1               5                  10                  15

Thr Pro Ser Gly Ala Glu Asp Leu Gln Arg Val Ala Ser Ser Arg Leu
             20                  25                  30

His Thr Thr Leu Leu Asp Ile Thr Asp Pro Gln Ser Val Gln Gln Ala
         35                  40                  45

Ala Lys Trp Val Glu Met His Val Lys Glu Ala Gly Leu Phe Gly Leu
     50                  55                  60

Val Asn Asn Ala Gly Val Ala Gly Ile Ile Gly Pro Thr Pro Trp Leu
 65                  70                  75                  80

Thr Arg Asp Asp Phe Gln Arg Val Leu Asn Val Asn Thr Met Gly Pro
                 85                  90                  95

Ile Gly Val Thr Leu Ala Leu Leu Pro Leu Leu Gln Gln Ala Arg Gly
            100                 105                 110

Arg Val Ile Asn Ile Thr Ser Val Leu Gly Arg Leu Ala Ala Asn Gly
        115                 120                 125

Gly Gly Tyr Cys Val Ser Lys Phe Gly Leu Glu Ala Phe Ser Asp Ser
    130                 135                 140
```

```
Leu Arg Arg Asp Val Ala His Phe Gly Ile Arg Val Ser Ile Val Glu
145                 150                 155                 160

Pro Gly Phe Phe Arg Thr Pro Val Thr Asn Leu Glu Ser Leu Glu Lys
                165                 170                 175

Thr Leu Gln Ala Cys Trp Ala Arg Leu Pro Pro Ala Thr Gln Ala His
            180                 185                 190

Tyr Gly Gly Ala Phe Leu Thr Lys Tyr Leu Lys Met Gln Gln Arg Ile
        195                 200                 205

Met Asn Leu Ile Cys Asp Pro Asp Leu Thr Lys Val Ser Arg Cys Leu
        210                 215                 220

Glu His Ala Leu Thr Ala Arg His Pro Arg Thr Arg Tyr Ser Pro Gly
225                 230                 235                 240

Trp Asp Ala Lys Leu Leu Trp Leu Pro Ala Ser Tyr Leu Pro Ala Ser
                245                 250                 255

Leu Val Asp Ala Val Leu Thr Trp Val Leu Pro Lys Pro Ala Gln Ala
                260                 265                 270

Val Tyr
```